US008691538B1

(12) United States Patent
Moll et al.

(10) Patent No.: US 8,691,538 B1
(45) Date of Patent: Apr. 8, 2014

(54) BIOFILM PHOTOBIOREACTOR SYSTEM AND METHOD OF USE

(71) Applicant: Algenol Biofuels Switzerland GmbH, Fort Myers, FL (US)

(72) Inventors: Benjamin Moll, Davis, CA (US); Benjamin McCool, Naples, FL (US); William Drake, Fort Myers, FL (US); William Porubsky, Fort Myers, FL (US); Ryan Adams, Fort Myers, FL (US); Heike Enke, Berlin (DE); Juliane Metzner, Berlin (DE); Karola Knuth, Berlin (DE)

(73) Assignee: Algenol Biofuels Switzerland GmbH, Fort Myers, FL (US)

( * ) Notice: Subject to any disclaimer, the term of this patent is extended or adjusted under 35 U.S.C. 154(b) by 0 days.

(21) Appl. No.: 13/631,478

(22) Filed: Sep. 28, 2012

(51) Int. Cl.
*C12P 7/56* (2006.01)
*C12P 7/06* (2006.01)
*C12P 7/02* (2006.01)

(52) U.S. Cl.
USPC ............................ 435/139; 435/161; 435/155

(58) Field of Classification Search
USPC ......................................... 435/139, 155, 161
See application file for complete search history.

(56) References Cited

U.S. PATENT DOCUMENTS

| 5,116,506 | A | 5/1992 | Williamson et al. |
| 5,595,893 | A | 1/1997 | Pometto, III et al. |
| 6,558,549 | B2 | 5/2003 | Cote et al. |
| 6,645,374 | B2 | 11/2003 | Cote et al. |
| 7,938,965 | B2 | 5/2011 | Rodgers et al. |
| 8,017,384 | B2 | 9/2011 | Tsai et al. |
| 8,058,058 | B2 | 11/2011 | Hickey et al. |
| 8,409,845 | B2 * | 4/2013 | Trent et al. ................. 435/257.1 |
| 2002/0020666 | A1 | 2/2002 | Cote et al. |
| 2003/0075501 | A1 | 4/2003 | Wilkie |
| 2003/0150798 | A1 | 8/2003 | Cote et al. |
| 2004/0079692 | A1 | 4/2004 | Cote et al. |
| 2004/0229343 | A1 | 11/2004 | Husain et al. |
| 2008/0160591 | A1 | 7/2008 | Willson et al. |
| 2009/0152195 | A1 | 6/2009 | Rodgers et al. |
| 2009/0181434 | A1 | 7/2009 | Aikens et al. |
| 2009/0258404 | A1 | 10/2009 | Mikkelsen et al. |
| 2009/0286296 | A1 | 11/2009 | Hickey et al. |
| 2012/0024798 | A1 | 2/2012 | Pickett et al. |

FOREIGN PATENT DOCUMENTS

| WO | 2012032109 | 3/2012 |
| WO | 2012083244 | 6/2012 |

* cited by examiner

*Primary Examiner* — Karen Cochrane Carlson
*Assistant Examiner* — Natalie Moss
(74) *Attorney, Agent, or Firm* — Lawrence B. Ebert; David J. Lorenz

(57) ABSTRACT

Flat panel biofilm photobioreactor systems with a photosynthetic, autofermentative microorganism that forms a biofilm and methods for using the same to make metabolic intermediate compound(s) through photosynthesis and to convert metabolic intermediate compound(s) into chemical product(s) such as a biofuel or a feedstock through autofermentation.

9 Claims, 13 Drawing Sheets

SEQUENCE LISTING

<160> NUMBER OF SEQ ID NOS: 16

<210> SEQ ID NO 1
<211> LENGTH: 1128
<212> TYPE: DNA
<213> ORGANISM: Geitlerinema sp.

<400> SEQUENCE: 1

```
ttgattgccg gtcgatcggt ctcatcagac acattggggc aactcgtccc gtatcctata        60
tttattaagt taaagtttgc aacgtcgaaa ctaatggtca cagaacgcac aatccccacg       120
tcctacagca atacggctga aatcagccgg gaagaagggc tgcgagtcta cgaagacatg       180
gttttagggc gcttcttcga ggacaagtgc gccgaaatgt actatcgcgg taaaatgttc       240
ggcttcgttc acctctacaa cggtcaagaa gccgtctcct ccggggtcat ccaagccatg       300
cgccccggcg acgattacgt ttgcagcacc taccgcgacc acgttcacgc tctcagttgc       360
ggtgttcccg cccgtgaagt gatggcgaa ctgttcggaa aatcgaccgg atgcagtaaa       420
gggcgcgggg ggtcgatgca tatgttctcg gaacccacc gactcctcgg cggttatgcg       480
tttgtcgctg aaggtattcc cgtggcgatg ggggcggcgt tccaagtgcg ctatcgcaag       540
gaagtcatgg gcgattcctc cgccgaccaa gtggtggcct gcttcttcgg cgacggtgcc       600
agtaacaacg gtcaattttt cgagaccttg aacatgcgt cgttgtggaa gctaccgatt       660
attttcgtcg tcgaaaacaa taaatgggcg atcgggatgg ctcacgaccg ggcgacctcg       720
caaccggaga tttacaaaaa agccagcgtg tttaacatgg ctggggtcga agtggatgga       780
atggacgtga tggcggtgcg ggcggcagcc caagaggcgg tcgatcgcgc gcgggccgga       840
gaaggcccca cgctcatcga ggcgttgacg taccgcttcc ggggacactc tctcgccgac       900
ccggacgaac tgcgatcgaa agaggagaag gaaatctggt tctctcgcga cccgattcac       960
cgctttgaaa actacctgac ggaagaaaac ctcgccagtg cggaggaact caaggacatt      1020
cagaagaaaa ttcaagaggt catcgacgac tcggtggaat tcgccgaatc cagccccgaa      1080
cccgacccca gcgaacttcg tcgctttatc tttgcagaag acgaataa                   1128
```

<210> SEQ ID NO 2
<211> LENGTH: 375
<212> TYPE: PRT
<213> ORGANISM: Geitlerinema sp.

<400> SEQUENCE: 2

```
Leu Ile Ala Gly Arg Ser Val Ser Ser Asp Thr Leu Gly Gln Leu Val
1               5                   10                  15

Pro Tyr Pro Ile Phe Ile Lys Leu Lys Phe Ala Thr Ser Lys Leu Met
            20                  25                  30

Val Thr Glu Arg Thr Ile Pro Thr Ser Tyr Ser Asn Thr Ala Glu Ile
        35                  40                  45

Ser Arg Glu Glu Gly Leu Arg Val Tyr Glu Asp Met Val Leu Gly Arg
50                  55                  60

Phe Phe Glu Asp Lys Cys Ala Glu Met Tyr Tyr Arg Gly Lys Met Phe
65                  70                  75                  80

Gly Phe Val His Leu Tyr Asn Gly Gln Glu Ala Val Ser Ser Gly Val
                85                  90                  95

Ile Gln Ala Met Arg Pro Gly Asp Asp Tyr Val Cys Ser Thr Tyr Arg
                100                 105                 110

Asp His Val His Ala Leu Ser Cys Gly Val Pro Ala Arg Glu Val Met
            115                 120                 125

Ala Glu Leu Phe Gly Lys Ser Thr Gly Cys Ser Lys Gly Arg Gly Gly
        130                 135                 140

Ser Met His Met Phe Ser Glu Pro His Arg Leu Leu Gly Gly Tyr Ala
145                 150                 155                 160

Phe Val Ala Glu Gly Ile Pro Val Ala Met Gly Ala Ala Phe Gln Val
                165                 170                 175

Arg Tyr Arg Lys Glu Val Met Gly Asp Ser Ser Ala Asp Gln Val Val
                180                 185                 190

Ala Cys Phe Phe Gly Asp Gly Ala Ser Asn Asn Gly Gln Phe Phe Glu
            195                 200                 205

Thr Leu Asn Met Ala Ser Leu Trp Lys Leu Pro Ile Ile Phe Val Val
210                 215                 220

Glu Asn Asn Lys Trp Ala Ile Gly Met Ala His Asp Arg Ala Thr Ser
225                 230                 235                 240

Gln Pro Glu Ile Tyr Lys Lys Ala Ser Val Phe Asn Met Ala Gly Val
                245                 250                 255

Glu Val Asp Gly Met Asp Val Met Ala Val Arg Ala Ala Ala Gln Glu
            260                 265                 270

Ala Val Asp Arg Ala Arg Ala Gly Glu Gly Pro Thr Leu Ile Glu Ala
        275                 280                 285

Leu Thr Tyr Arg Phe Arg Gly His Ser Leu Ala Asp Pro Asp Glu Leu
290                 295                 300

Arg Ser Lys Glu Glu Lys Glu Ile Trp Phe Ser Arg Asp Pro Ile His
305                 310                 315                 320

Arg Phe Glu Asn Tyr Leu Thr Glu Glu Asn Leu Ala Ser Ala Glu Glu
                325                 330                 335

Leu Lys Asp Ile Gln Lys Lys Ile Gln Glu Val Ile Asp Asp Ser Val
            340                 345                 350

Glu Phe Ala Glu Ser Ser Pro Glu Pro Asp Pro Ser Glu Leu Arg Arg
        355                 360                 365

Phe Ile Phe Ala Glu Asp Glu
370                 375

<210> SEQ ID NO 3
<211> LENGTH: 984
<212> TYPE: DNA
<213> ORGANISM: Geitlerinema sp.

<400> SEQUENCE: 3
```

```
atggcagaaa ccttattttt caacgcttta agagaagcca tcgacgaaga aatggcgcga    60
gacgagaccg tcttcgtcct cggagaggat gtcggtcact acggcggttc ctacaaagtt   120
accaaagacc tctatcaaaa atacggcgaa ctgcgcctgc tcgacacgcc catcgccgaa   180
aacagtttca cggggatggc cgtaggtgcg gcgattacag ggttgcgacc catcatcgaa   240
ggcatgaaca tggggtttct gctcctggcc ttcaaccaaa tcgccaataa tgccgggatg   300
ttgcgctaca cctccggcgg aaacttcaaa attcccatgg tgattcgcgg tccgggtggc   360
gtcggacgcc aactcggtgc cgaacactct caacggctcg aagcgtactt tcaagccgtt   420
ccggggttga aaatcgtcgc ttgttcgacc ccgtacaacg cgaaaggttt gctcaaagcc   480
gctattcgcg acaacaaccc agtattgttc ttcgaacacg tgctgctcta acctcaaa    540
gaaaacttac ccgagagcga atacgtcgtt cccctcgata aagccgaagt ggtgcgagac   600
ggaaaagacg tgacgatttt gacctactcg cggatgcgcc accactgcac gcaagcggca   660
aaaaccttag aaaagacggg ttcgatcccc gaaattatcg acttgatttc cctcaagccc   720
tacgacctcg aaaccatcgg aaattcgatt cgcaaaaccc accgcgttat cgtcgtcgaa   780
gaatgtatga aaactggcgg tgtcggtgcc gaactgatcg ccaccatcaa cgaccatttc   840
ttcgacgaac tcgacgcccc cgtgattcgt ttgtcctccc aagacattcc gacgccctat   900
aacggaatgc tcgaacggtt gacgatcgtg caaccgcatc aaatcgtcga agcggttcag   960
aacatggtgg cgttaaaagt gtag                                          984
```

<210> SEQ ID NO 4
<211> LENGTH: 327
<212> TYPE: PRT
<213> ORGANISM: Geitlerinema sp.

<400> SEQUENCE: 4

```
Met Ala Glu Thr Leu Phe Phe Asn Ala Leu Arg Glu Ala Ile Asp Glu
1               5                   10                  15

Glu Met Ala Arg Asp Glu Thr Val Phe Val Leu Gly Glu Asp Val Gly
            20                  25                  30

His Tyr Gly Gly Ser Tyr Lys Val Thr Lys Asp Leu Tyr Gln Lys Tyr
        35                  40                  45

Gly Glu Leu Arg Leu Leu Asp Thr Pro Ile Ala Glu Asn Ser Phe Thr
    50                  55                  60

Gly Met Ala Val Gly Ala Ala Ile Thr Gly Leu Arg Pro Ile Ile Glu
65                  70                  75                  80

Gly Met Asn Met Gly Phe Leu Leu Leu Ala Phe Asn Gln Ile Ala Asn
                85                  90                  95

Asn Ala Gly Met Leu Arg Tyr Thr Ser Gly Gly Asn Phe Lys Ile Pro
            100                 105                 110

Met Val Ile Arg Gly Pro Gly Val Gly Arg Gln Leu Gly Ala Glu
        115                 120                 125

His Ser Gln Arg Leu Glu Ala Tyr Phe Gln Ala Val Pro Gly Leu Lys
    130                 135                 140

Ile Val Ala Cys Ser Thr Pro Tyr Asn Ala Lys Gly Leu Leu Lys Ala
145                 150                 155                 160

Ala Ile Arg Asp Asn Asn Pro Val Leu Phe Phe Glu His Val Leu Leu
                165                 170                 175

Tyr Asn Leu Lys Glu Asn Leu Pro Glu Ser Glu Tyr Val Val Pro Leu
            180                 185                 190

Asp Lys Ala Glu Val Val Arg Asp Gly Lys Asp Val Thr Ile Leu Thr
        195                 200                 205
```

```
Tyr Ser Arg Met Arg His His Cys Thr Gln Ala Ala Lys Thr Leu Glu
    210                 215                 220
Lys Asp Gly Phe Asp Pro Glu Ile Ile Asp Leu Ile Ser Leu Lys Pro
225                 230                 235                 240
Tyr Asp Leu Glu Thr Ile Gly Asn Ser Ile Arg Lys Thr His Arg Val
                245                 250                 255
Ile Val Val Glu Glu Cys Met Lys Thr Gly Gly Val Gly Ala Glu Leu
            260                 265                 270
Ile Ala Thr Ile Asn Asp His Phe Phe Asp Glu Leu Asp Ala Pro Val
        275                 280                 285
Ile Arg Leu Ser Ser Gln Asp Ile Pro Thr Pro Tyr Asn Gly Met Leu
    290                 295                 300
Glu Arg Leu Thr Ile Val Gln Pro His Gln Ile Val Glu Ala Val Gln
305                 310                 315                 320
Asn Met Val Ala Leu Lys Val
                325

<210> SEQ ID NO 5
<211> LENGTH: 1323
<212> TYPE: DNA
<213> ORGANISM: Geitlerinema sp.

<400> SEQUENCE: 5
atgatccacg aaatcttcat gcctgcccta agttccacca tgactgaagg caaaatcgtc     60
tcttggacga atccccagg ggacaaggtg aaaaaggcg aaacggtggt tgtcgtcgag    120
tcggacaaag ctgacatgga cgtggagtcc ttctacgaag ggattctggc gaccatcgtt    180
gtcggagaag cgacgtcgc ccccgtcggc ggaaccatcg ccctgttagc cgaaacggaa    240
gcggaaatcg aagaagctaa gcaaaaagcc cagcaacagc aacaagggca ccccaaacg    300
gcggccgctt cggaaacgcc gtcaaccccc caaccgactc cagccgcagc gacggcacaa    360
aacggcgcgt ctcaagcggc ggccagcgga caaaatggcg gacgcattgt cgcctctcct    420
cgcgcccgga gttagccaa agagctgaaa gtcgatttga acgggttgca cgggagcggt    480
ccttacggtc gtatcgtggc tgaagacgtg caagcagcgg ccggacaacc cgtcctaccg    540
actgcaacgg cagttgcacc gatgccctca gctcccgctc cgtcggcagt tccctcggtt    600
ccggcgcaag cccccacgac aacggctccg gctgccacta gcgcccccctt gggtcaggtg    660
gttccgttca atacgctgca aggggcagtg gtgcggaaca tgacggcgag tttgcaagtg    720
ccgacgttcc acgtgggtta ccatcatcacc acggacaatt tagacgcctt ataccagcaa    780
attaagtcca aggtgtgac gatgacgggg ctactggcga agccgtggc ggtgacgttg    840
cagaaacacc cgttacttta cgccagctac accgaacagg gcgttcagta caacagcaac    900
attaacgtgg cggtggcggt ggccatgccc ggaggcggct tgattacgcc ggtgatgcgc    960
gatgccgacc agatggatat ttactcgctg tctcggtcgt ggaaggatct cgtggcgcga   1020
tcgcgtgcca acaactgca accggaagag tacagcacgg gaacctttac cctgtccaat   1080
ttgggaatgc tcggggtcga tcgcttcgat gcgattttac ccccggaca aggatcgatt   1140
ctcgcgatcg gtgcctctcg tccccaggtt gtcgccacgg acgacggcat gatgggcgtc   1200
aaacgtcaaa tgcaagtgaa cattacctgc gaccaccgca ttatttacgg tgcagacgcg   1260
gcggcgttct tgaaagattt ggccgacctc gttgaaaaca cccgcaatc tctaacgctg   1320
taa                                                               1323
```

-continued

```
<210> SEQ ID NO 6
<211> LENGTH: 440
<212> TYPE: PRT
<213> ORGANISM: Geitlerinema sp.

<400> SEQUENCE: 6

Met Ile His Glu Ile Phe Met Pro Ala Leu Ser Ser Thr Met Thr Glu
1               5                   10                  15

Gly Lys Ile Val Ser Trp Thr Lys Ser Pro Gly Asp Lys Val Glu Lys
            20                  25                  30

Gly Glu Thr Val Val Val Glu Ser Asp Lys Ala Asp Met Asp Val
        35                  40                  45

Glu Ser Phe Tyr Glu Gly Ile Leu Ala Thr Ile Val Val Gly Glu Gly
    50                  55                  60

Asp Val Ala Pro Val Gly Gly Thr Ile Ala Leu Leu Ala Glu Thr Glu
65                  70                  75                  80

Ala Glu Ile Glu Glu Ala Lys Gln Lys Ala Gln Gln Gln Gln Gln Gly
                85                  90                  95

Gln Pro Gln Thr Ala Ala Ala Ser Glu Thr Pro Ser Thr Pro Gln Pro
            100                 105                 110

Thr Pro Ala Ala Ala Thr Ala Gln Asn Gly Ala Ser Gln Ala Ala Ala
        115                 120                 125

Ser Gly Gln Asn Gly Gly Arg Ile Val Ala Ser Pro Arg Ala Arg Lys
    130                 135                 140

Leu Ala Lys Glu Leu Lys Val Asp Leu Asn Gly Leu His Gly Ser Gly
145                 150                 155                 160

Pro Tyr Gly Arg Ile Val Ala Glu Asp Val Gln Ala Ala Gly Gln
                165                 170                 175

Pro Val Leu Pro Thr Ala Thr Ala Val Ala Pro Met Pro Ser Ala Pro
            180                 185                 190

Ala Pro Ser Ala Val Pro Ser Val Pro Ala Gln Ala Pro Thr Thr Thr
        195                 200                 205

Ala Pro Ala Ala Thr Ser Ala Pro Leu Gly Gln Val Val Pro Phe Asn
    210                 215                 220

Thr Leu Gln Gly Ala Val Val Arg Asn Met Thr Ala Ser Leu Gln Val
225                 230                 235                 240

Pro Thr Phe His Val Gly Tyr Thr Ile Thr Thr Asp Asn Leu Asp Ala
                245                 250                 255

Leu Tyr Gln Gln Ile Lys Ser Lys Gly Val Thr Met Thr Gly Leu Leu
            260                 265                 270

Ala Lys Ala Val Ala Val Thr Leu Gln Lys His Pro Leu Leu Tyr Ala
        275                 280                 285

Ser Tyr Thr Glu Gln Gly Val Gln Tyr Asn Ser Asn Ile Asn Val Ala
    290                 295                 300

Val Ala Val Ala Met Pro Gly Gly Leu Ile Thr Pro Val Met Arg
305                 310                 315                 320

Asp Ala Asp Gln Met Asp Ile Tyr Ser Leu Ser Arg Ser Trp Lys Asp
                325                 330                 335

Leu Val Ala Arg Ser Arg Ala Lys Gln Leu Gln Pro Glu Glu Tyr Ser
            340                 345                 350

Thr Gly Thr Phe Thr Leu Ser Asn Leu Gly Met Leu Gly Val Asp Arg
        355                 360                 365

Phe Asp Ala Ile Leu Pro Pro Gly Gln Gly Ser Ile Leu Ala Ile Gly
    370                 375                 380

Ala Ser Arg Pro Gln Val Val Ala Thr Asp Asp Gly Met Met Gly Val
```

```
385                 390                 395                 400
Lys Arg Gln Met Gln Val Asn Ile Thr Cys Asp His Arg Ile Ile Tyr
                405                 410                 415
Gly Ala Asp Ala Ala Ala Phe Leu Lys Asp Leu Ala Asp Leu Val Glu
                420                 425                 430
Asn Asn Pro Gln Ser Leu Thr Leu
                435                 440

<210> SEQ ID NO 7
<211> LENGTH: 875
<212> TYPE: DNA
<213> ORGANISM: Geitlerinema sp.

<400> SEQUENCE: 7
atggcaaaga ttcaggctta tgctgcccga gacgtggcgg aaaaactcga accgtttgaa      60
tacgatcccg gtgcgttgga tgccgaagag gtcgaactcg ctgtcgaatc ctgcgggatc     120
tgtcacagcg acctgagtat gttagacgac gaatgggaga tgacgcaata tcccttcgtt     180
cccggtcacg aagtcgtcgg aaccgtgacg gagatcggcg atcgcgtcac cgatctccaa     240
atcggacagc gggtcggttt gggctggttt gccaactcct gtatggggtt gccagtggtgt    300 atgtccggcg accacaatct ctgtagcgac gccgaaggca cgatcgtcgg acgtcacggc     360
ggatttgccg atcgcgttcg cgcccatcac agttgggtca tcccgattcc cgagggcatc     420
gatcccctca aggccgggcc gctgttctgc ggtggcatta ccgtattcaa tccgatggta     480
gagttcgacc tcaaacccac cgatcgcgtg gtgtgtggtgg aattggcgg cctcggacac     540 ctggcgattc aattcctcag tgcttgggga tgcgaggtga cggcgttctc gacgagtgcg     600
gacaaggaag ccgaagccaa agaactcggg gcgaccccat ttgtcaattc taaagatctc     660
gacgccctgc aagcggtcga aaactccttt gattttatta tttcgacggt gagtgccgat     720
ctcgattgga cgcttacgt ggcggcgttg cgaccgaagg gacgattgca cttagttggc     780
gtggcgacga atcccctcga tttacagttg tttcctctgc tgatgggtca gaagtcggtg     840
tcgtcgagtc cggtggggag tccggtgacg atcgc                                875

<210> SEQ ID NO 8
<211> LENGTH: 291
<212> TYPE: PRT
<213> ORGANISM: Geitlerinema sp.

<400> SEQUENCE: 8

Met Ala Lys Ile Gln Ala Tyr Ala Ala Arg Asp Val Ala Gly Lys Leu
1               5                   10                  15
Glu Pro Phe Glu Tyr Asp Pro Gly Ala Leu Asp Ala Glu Glu Val Glu
                20                  25                  30
Leu Ala Val Glu Ser Cys Gly Ile Cys His Ser Asp Leu Ser Met Leu
            35                  40                  45
Asp Asp Glu Trp Glu Met Thr Gln Tyr Pro Phe Val Pro Gly His Glu
        50                  55                  60
Val Val Gly Thr Val Thr Glu Ile Gly Asp Arg Val Thr Asp Leu Gln
65                  70                  75                  80
Ile Gly Gln Arg Val Gly Leu Gly Trp Phe Ala Asn Ser Cys Met Gly
                85                  90                  95
Cys Gln Trp Cys Met Ser Gly Asp His Asn Leu Cys Ser Asp Ala Glu
            100                 105                 110
Gly Thr Ile Val Gly Arg His Gly Gly Phe Ala Asp Arg Val Arg Ala
        115                 120                 125
```

```
His His Ser Trp Val Ile Pro Ile Pro Glu Gly Ile Asp Pro Leu Lys
    130                 135                 140

Ala Gly Pro Leu Phe Cys Gly Gly Ile Thr Val Phe Asn Pro Met Val
145                 150                 155                 160

Glu Phe Asp Leu Lys Pro Thr Asp Arg Val Gly Val Gly Ile Gly
                165                 170                 175

Gly Leu Gly His Leu Ala Ile Gln Phe Leu Ser Ala Trp Gly Cys Glu
            180                 185                 190

Val Thr Ala Phe Ser Thr Ser Ala Asp Lys Glu Ala Glu Ala Lys Glu
        195                 200                 205

Leu Gly Ala Thr His Phe Val Asn Ser Lys Asp Leu Asp Ala Leu Gln
    210                 215                 220

Ala Val Glu Asn Ser Phe Asp Phe Ile Ile Ser Thr Val Ser Ala Asp
225                 230                 235                 240

Leu Asp Trp Asn Ala Tyr Val Ala Ala Leu Arg Pro Lys Gly Arg Leu
                245                 250                 255

His Leu Val Gly Val Ala Thr Asn Pro Leu Asp Leu Gln Leu Phe Pro
            260                 265                 270

Leu Leu Met Gly Gln Lys Ser Val Ser Ser Pro Val Gly Ser Pro
        275                 280                 285

Val Thr Ile
    290

<210> SEQ ID NO 9
<211> LENGTH: 1587
<212> TYPE: DNA
<213> ORGANISM: Geitlerinema sp.

<400> SEQUENCE: 9
ttgatgggta ttgcagcaga gaaactcgcc ccaatttcga tcgtgttgtt tgccgccgga      60
attttaatct gggggtatta ccgcgctcga ccctacggca aaatcggctt gctgtcttgg     120
ttgcagtcgg tttctgtcac agctccctgg ctgctgtttt cgccctgttt ctcagccggg     180
attttcatca atttcgcagg cgtgttgttc ctcatcgtcg cgtccgtttt aacttacatc     240
gggctgggac gacaactgcg agcggcggct cgagatcccg aacaacgagc gtacttagaa     300
aaactcgcga acgcccaacg gtcttcaaaa tctgacgagt cctctcaaac ttccgatctt     360
gccgaaccgt ccgaagactc tgaagcggcc gaaccgtctc cggacaccgc acgaccgacg     420
gagccagttg ccgcctctgt ccgagatcgc gatcgagaaa gcgatcgccc gtttcagaac     480
ctatccgttc cggaggacga cttacactgc attcaagaaa tcttcggaat cgatacgttt     540
ttcgccacag agacgatccc gtaccagtcg ggagcaattt tcaaaggcaa ccttcgggga     600
gaggtcgaag cgacccatca ggaactgtcg aaaaagctgc acgatcgcgt gggcgatcgc     660
taccgtttgt ttttcgtcaa cgatcccgac gaaaaaacgg tcgtcgtcgt cttgccgagt     720
cgtaacgacc ctcaaccgct cacgacgaac caacagattt tagcggtcgt attgttcgtc     780
gcgacgatcg tcaccactct cgaaaccggg ggggcatttc tcggattcga cttgttcgag     840
aatttaaacc gctggacgga aacactgccc ctcgccttgg aatttgggc gatattgctc     900
gttcacgaac tcgccaccg tatcgcggcc ggacgtatg gcattgcgct ctcgccgcca     960
ttttccttc ccacctggca aatcggctct tcggtgcga ttacccgttt cgagtcgttg    1020
ctgcccaacc gttcgaccct gttcgacatc gccatcgccg gccggccgc cggtgggttg    1080
ttgtccttgg gaatgttagc ggtcgggttc gttctgtccc acgacgggag tttgtttcaa    1140
```

```
cttccgagcg aatttttccg agggtcggtt ttggtgggat tgctggccaa ggcgttttta   1200
ggtgaagccc tccagcagag tttggtagac gtgcatccgt tggtcgttct cggttggctg   1260
gggttagtca ttaacgccct caacctgatt ccagccggac agttagacgg cgggcgcgtc   1320
atgcaggcga tttacggtcg tcggattgcg gggcgatcga cgatcgccac cctcatcgtg   1380
ttagcgatcg cttccttcgt caatccgtta gccttgtact gggcgatcgt gattttggtc   1440
atccaacggg atttagagcg tccgagtctc aacgaaatta ccgaacccga cgacacccgt   1500
gcaattttgg cgttcgtggc actgttggtc atgttgatga cgttgattcc ctttacgccg   1560
agtttggcgt tgcgcctggg gctgtaa                                       1587
```

<210> SEQ ID NO 10
<211> LENGTH: 528
<212> TYPE: PRT
<213> ORGANISM: Geitlerinema sp.

<400> SEQUENCE: 10

```
Leu Met Gly Ile Ala Ala Glu Lys Leu Ala Pro Ile Ser Ile Val Leu
 1               5                  10                  15

Phe Ala Ala Gly Ile Leu Ile Trp Gly Tyr Tyr Arg Ala Arg Pro Tyr
             20                  25                  30

Gly Lys Ile Gly Leu Leu Ser Trp Leu Gln Ser Val Ser Val Thr Ala
         35                  40                  45

Pro Trp Leu Leu Phe Phe Ala Leu Phe Ser Ala Gly Ile Phe Ile Asn
     50                  55                  60

Phe Ala Gly Val Leu Phe Leu Ile Val Ala Ser Val Leu Thr Tyr Ile
 65                  70                  75                  80

Gly Leu Gly Arg Gln Leu Arg Ala Ala Ala Arg Asp Pro Glu Gln Arg
                 85                  90                  95

Ala Tyr Leu Glu Lys Leu Ala Asn Ala Gln Arg Ser Ser Lys Ser Asp
            100                 105                 110

Glu Ser Ser Gln Thr Ser Asp Leu Ala Glu Pro Ser Glu Asp Ser Glu
        115                 120                 125

Ala Ala Glu Pro Ser Pro Asp Thr Ala Arg Pro Thr Glu Pro Val Ala
    130                 135                 140

Ala Ser Val Arg Asp Arg Asp Arg Glu Ser Asp Arg Pro Phe Gln Asn
145                 150                 155                 160

Leu Ser Val Pro Glu Asp Asp Leu His Cys Ile Gln Glu Ile Phe Gly
                165                 170                 175

Ile Asp Thr Phe Phe Ala Thr Glu Thr Ile Pro Tyr Gln Ser Gly Ala
            180                 185                 190

Ile Phe Lys Gly Asn Leu Arg Gly Glu Val Glu Ala Thr His Gln Glu
        195                 200                 205

Leu Ser Lys Lys Leu His Asp Arg Val Gly Asp Arg Tyr Arg Leu Phe
    210                 215                 220

Phe Val Asn Asp Pro Asp Glu Lys Thr Val Val Val Leu Pro Ser
225                 230                 235                 240

Arg Asn Asp Pro Gln Pro Leu Thr Thr Asn Gln Gln Ile Leu Ala Val
                245                 250                 255

Val Leu Phe Val Ala Thr Ile Val Thr Thr Leu Glu Thr Gly Gly Ala
            260                 265                 270

Phe Leu Gly Phe Asp Leu Phe Glu Asn Leu Asn Arg Trp Thr Glu Thr
        275                 280                 285

Leu Pro Leu Ala Leu Gly Ile Trp Ala Ile Leu Leu Val His Glu Leu
    290                 295                 300
```

-continued

Gly His Arg Ile Ala Ala Gly Arg Tyr Gly Ile Ala Leu Ser Pro Pro
305                 310                 315                 320

Phe Phe Leu Pro Thr Trp Gln Ile Gly Ser Phe Gly Ala Ile Thr Arg
            325                 330                 335

Phe Glu Ser Leu Leu Pro Asn Arg Ser Thr Leu Phe Asp Ile Ala Ile
            340                 345                 350

Ala Gly Pro Ala Ala Gly Gly Leu Leu Ser Leu Gly Met Leu Ala Val
            355                 360                 365

Gly Phe Val Leu Ser His Asp Gly Ser Leu Phe Gln Leu Pro Ser Glu
        370                 375                 380

Phe Phe Arg Gly Ser Val Leu Val Gly Leu Leu Ala Lys Ala Phe Leu
385                 390                 395                 400

Gly Glu Ala Leu Gln Gln Ser Leu Val Asp Val His Pro Leu Val Val
            405                 410                 415

Leu Gly Trp Leu Gly Leu Val Ile Asn Ala Leu Asn Leu Ile Pro Ala
            420                 425                 430

Gly Gln Leu Asp Gly Gly Arg Val Met Gln Ala Ile Tyr Gly Arg Arg
        435                 440                 445

Ile Ala Gly Arg Ser Thr Ile Ala Thr Leu Ile Val Leu Ala Ile Ala
450                 455                 460

Ser Phe Val Asn Pro Leu Ala Leu Tyr Trp Ala Ile Val Ile Leu Val
465                 470                 475                 480

Ile Gln Arg Asp Leu Glu Arg Pro Ser Leu Asn Glu Ile Thr Glu Pro
            485                 490                 495

Asp Asp Thr Arg Ala Ile Leu Ala Phe Val Ala Leu Leu Val Met Leu
            500                 505                 510

Met Thr Leu Ile Pro Phe Thr Pro Ser Leu Ala Leu Arg Leu Gly Leu
        515                 520                 525

<210> SEQ ID NO 11
<211> LENGTH: 1849
<212> TYPE: DNA
<213> ORGANISM: Geitlerinema sp.

<400> SEQUENCE: 11
atgtcagaac agacgataga atcaattctt cacgagcaac ggacgttttcc cccagccgca        60 gattttgccg ctaacgccca tatcaaaagc atggccgact ataaggcttt gtgcgatcgc       120
gccgaaaaag acccggctgg attttggagc gaactggccg aaaccgaact cgactggttt       180
caaaagtggg agaacgtcct cgactggcaa cccccgttg ccaaatggtt cgagggaggc        240
aaactcaacg tttcttacaa ctgcctcgat cgccatctga ccacctggcg caaaaacaaa       300
gccgcgttga tttgggaagg ggaacctggc gactcgcgca ccctcaccta cgcccaactg       360
caccgcgaag tgtgccagat ggccaacgtc atcaaacagt tcggcgtgaa aaaaggcgat       420
gtcgtgggga tttatatgcc catgattccc gaagcggcga tcgccatgtt agcctgcgcc       480
cgcatcggtg ccgttcacag cgtcgtgttc ggtggcttca gtgccgaagc cctgcgcgat       540
cgcgtcaacg ccgccgaagc caaactgtg attaccgccg acggcggctt ccgcaaagac       600
aaagtcgtca ccctcaaaga ccaagtcgat aaagccctcg ccaacgacgc cgcccccagc       660
gtcgaaaacg ttctcgtggt gcgtcgcatc gaaaaagaca ctcacatgga agagggtcgg       720
gaccactggt ggcacgaagt ccgtcaaggc atctccgccc actgtcctgc gaaccgatg        780 gacagcgaag acatcctttt catcctctac accagcggca gcaccggaaa accgaaaggc       840
gtcgttcaca ccaccgccgg atacaacctc tacgcccacg tcaccaacaa atggacgttc       900

```
gacctgaagg acaccgatat tttctggtgt accgccgacg tgggttggat taccggacac    960
agctatatcg tctacggtcc gctgtctaac ggggcgacga cggtgatgta cgaagggatt   1020
ccccgtccgt ccaaccccgg ctgttttttgg gatgtcgtgg aaaaatacgg cgtcacgatt  1080
ttctacaccg ccccaccgc cattcgtgcc tttattaaag ccggagacaa acacccgaac    1140
gcccgcgatt tgtccagctt gcggctgttg ggaaccgtgg gcgaacccat caacccgaaa   1200
gcctggatgt ggtatcaccg agtcatcggc ggcgaacgct gtccggtcgt cgatacctgg   1260
tggcagacgg aaacgggcgg tttcatgatt acgccgctac cggggggcgac gccgacgaaa  1320
cccggttcgg caacgctgcc gttccctggt attcaagcgg acgtgctgga tttggacgga   1380
aacgaaattc cggcgaacca gggggatat ttggtcgtca acatccctg gccgggcatg     1440
atgcggacgg tttacggaga ctttaaccgt tttcgccgca gctattggga gcatattgct   1500
ccgaaagacg gtcagtattt ctattttgcc ggagacggcg ctcgcaagga cgaggacggc   1560
tatttctgga ttatgggtcg cgtggacgac gtgatcaacg tttcgggaca tcgcctcggg   1620
acgatggaaa tcgagtcggc gttggtgtcg cacccgtcag tggcggaagc ggcggtggtc   1680
gggaagccgg acgagattaa gggtgaaagc atcgtggcgt tcgtgatgtt ggaggaggac   1740
tacgaggctg cgacgacttt ggataaggcg ttgaagcagc acgtggttga ggaaatcggc   1800
gcgatcgccc gtccgggtga gattcgtttt tcagaagatt tgccgaaaa              1849

<210> SEQ ID NO 12
<211> LENGTH: 616
<212> TYPE: PRT
<213> ORGANISM: Geitlerinema sp.

<400> SEQUENCE: 12

Met Ser Glu Gln Thr Ile Glu Ser Ile Leu His Glu Gln Arg Thr Phe
1               5                   10                  15

Pro Pro Ala Ala Asp Phe Ala Ala Asn Ala His Ile Lys Ser Met Ala
            20                  25                  30

Asp Tyr Lys Ala Leu Cys Asp Arg Ala Glu Lys Asp Pro Ala Gly Phe
        35                  40                  45

Trp Ser Glu Leu Ala Glu Thr Glu Leu Asp Trp Phe Gln Lys Trp Glu
    50                  55                  60

Asn Val Leu Asp Trp Gln Pro Pro Val Ala Lys Trp Phe Glu Gly Gly
65                  70                  75                  80

Lys Leu Asn Val Ser Tyr Asn Cys Leu Asp Arg His Leu Thr Thr Trp
                85                  90                  95

Arg Lys Asn Lys Ala Ala Leu Ile Trp Glu Gly Glu Pro Gly Asp Ser
            100                 105                 110

Arg Thr Leu Thr Tyr Ala Gln Leu His Arg Glu Val Cys Gln Met Ala
        115                 120                 125

Asn Val Ile Lys Gln Phe Gly Val Lys Gly Asp Val Val Gly Ile
    130                 135                 140

Tyr Met Pro Met Ile Pro Glu Ala Ala Ile Ala Met Leu Ala Cys Ala
145                 150                 155                 160

Arg Ile Gly Ala Val His Ser Val Val Phe Gly Gly Phe Ser Ala Glu
                165                 170                 175

Ala Leu Arg Asp Arg Val Asn Ala Ala Glu Ala Lys Leu Val Ile Thr
            180                 185                 190

Ala Asp Gly Gly Phe Arg Lys Asp Lys Val Val Thr Leu Lys Asp Gln
        195                 200                 205
```

Val Asp Lys Ala Leu Ala Asn Asp Ala Ala Pro Ser Val Glu Asn Val
210                 215                 220

Leu Val Val Arg Arg Ile Glu Lys Asp Thr His Met Glu Glu Gly Arg
225                 230                 235                 240

Asp His Trp Trp His Glu Val Arg Gln Gly Ile Ser Ala His Cys Pro
            245                 250                 255

Ala Glu Pro Met Asp Ser Glu Asp Ile Leu Phe Ile Leu Tyr Thr Ser
            260                 265                 270

Gly Ser Thr Gly Lys Pro Lys Gly Val Val His Thr Thr Ala Gly Tyr
        275                 280                 285

Asn Leu Tyr Ala His Val Thr Asn Lys Trp Thr Phe Asp Leu Lys Asp
290                 295                 300

Thr Asp Ile Phe Trp Cys Thr Ala Asp Val Gly Trp Ile Thr Gly His
305                 310                 315                 320

Ser Tyr Ile Val Tyr Gly Pro Leu Ser Asn Gly Ala Thr Thr Val Met
                325                 330                 335

Tyr Glu Gly Val Pro Arg Pro Ser Asn Pro Gly Cys Phe Trp Asp Val
                340                 345                 350

Val Glu Lys Tyr Gly Val Thr Ile Phe Tyr Thr Ala Pro Thr Ala Ile
            355                 360                 365

Arg Ala Phe Ile Lys Ala Gly Asp Lys His Pro Asn Ala Arg Asp Leu
370                 375                 380

Ser Ser Leu Arg Leu Leu Gly Thr Val Gly Glu Pro Ile Asn Pro Lys
385                 390                 395                 400

Ala Trp Met Trp Tyr His Arg Val Ile Gly Gly Glu Arg Cys Pro Val
                405                 410                 415

Val Asp Thr Trp Trp Gln Thr Glu Thr Gly Gly Phe Met Ile Thr Pro
            420                 425                 430

Leu Pro Gly Ala Thr Pro Thr Lys Pro Gly Ser Ala Thr Leu Pro Phe
        435                 440                 445

Pro Gly Ile Gln Ala Asp Val Leu Asp Leu Asp Gly Asn Glu Ile Pro
    450                 455                 460

Ala Asn Gln Gly Gly Tyr Leu Val Val Lys His Pro Trp Pro Gly Met
465                 470                 475                 480

Met Arg Thr Val Tyr Gly Asp Phe Asn Arg Phe Arg Arg Ser Tyr Trp
                485                 490                 495

Glu His Ile Ala Pro Lys Asp Gly Gln Tyr Phe Tyr Phe Ala Gly Asp
                500                 505                 510

Gly Ala Arg Lys Asp Glu Asp Gly Tyr Phe Trp Ile Met Gly Arg Val
            515                 520                 525

Asp Asp Val Ile Asn Val Ser Gly His Arg Leu Gly Thr Met Glu Ile
530                 535                 540

Glu Ser Ala Leu Val Ser His Pro Ser Val Ala Glu Ala Ala Val Val
545                 550                 555                 560

Gly Lys Pro Asp Glu Ile Lys Gly Glu Ser Ile Val Ala Phe Val Met
            565                 570                 575

Leu Glu Glu Asp Tyr Glu Ala Gly Asp Asp Leu Asp Lys Ala Leu Lys
            580                 585                 590

Gln His Val Val Glu Glu Ile Gly Ala Ile Ala Arg Pro Gly Glu Ile
            595                 600                 605

Arg Phe Ser Glu Asp Leu Pro Lys
610                 615

<210> SEQ ID NO 13

<211> LENGTH: 1410
<212> TYPE: DNA
<213> ORGANISM: Geitlerinema sp.

<400> SEQUENCE: 13

```
atggaatcgg tgcaaactcc atcgccgcag actccatcgt cagtcgccga tcgcgtccga      60
gcgcaacggg cgttcttcgc gacgggcaaa accaaagacg taaatttccg cctcgaacaa     120
ctcaaacgcc tcaaacacgc gattctcgac taccgagacc gaatcgtcga agcagtcggg     180
gctgacttgc gccgccggaa atttgaagcc tatttcgaga tcgcctccat cgccgaagtc     240
aacaccgcga tcgcacgcct gaaatcttgg gcgaaaccca acgggtatc cacctctctc     300
gatcagtttc cgtctcgcgc ccgcattcac cccgaaccgt gggcgtcgt gctaatcgtc     360
gccccctgga actacccgtt tcaactgacg atgagtcccc tcgtcggcgc gatcgcggcc     420
ggaaattgcg ccgttctcaa accctcggaa attgccccc acaccgcagc gtcgtcagt     480
gacttgattc gctcgacctt tccccctgaa tacgtcaccg ccatcgaagg cggcgtcgaa     540
accagtcaat ccctcctcga acagaaattc gacaaaatct tttttaccgg gggaacccgc     600
atcggccaga tcgtcatgga agcggcggcg aaacacctca ccccgttac cctggaactc     660
ggcggaaaaa gcccctgtat cgtcgatgcg gacgtgaaac tcgacgttgc tgtcaaacgc     720
atcgtttggg gaaagtttat caacgccgga caaacctgtg tcgcgccgga ttacctgctc     780
gtcgatcgcc gcgttaaacc ccgactgctc gaagcggtgc gccagcaagt ccgcgagttt     840
tttggcgacg atcccgccaa aagtgccgat ttctgtcgca tggtaagcga tcgccatttc     900
gatcgcgtcg cctcgttact agaaaatcgg ggaaatgctg agattgtcgt cggcggacag     960
tgcgatcgca gcgatcgcta catcgccccc accgtcctcg ataacgtatc ctggaacgat    1020
ccggtgatgc aagacgaaat tttcggcccg attctgcccg ttttagagta cgacagtctc    1080
gacgacgcca tcgatcgcgt cgcttcccgt cccaaacccc tcgccctcta cgtctttct    1140
aacaacaaac ccttccaaaa ccgcgtcttg cgcgagactt cctccggcgg agcctgcgtc    1200
aacgatactg tcatgcacct ggccgttttcc gatctcccct ttggcggcgt cggcgacagc    1260
ggaatgggaa gctatcacgg aaaagccagt ttcgatacct tctcccattt caaaagcgtc    1320
ctcaacaaag gactttggtt cgatctcaac tggcgttacg cgccctatca tcaatggcaa    1380
ctcagccttc tcaaacgcat catcggttga                                     1410
```

<210> SEQ ID NO 14
<211> LENGTH: 469
<212> TYPE: PRT
<213> ORGANISM: Geitlerinema sp.

<400> SEQUENCE: 14

```
Met Glu Ser Val Gln Thr Pro Ser Pro Gln Thr Pro Ser Ser Val Ala
1               5                   10                  15

Asp Arg Val Arg Ala Gln Arg Ala Phe Phe Ala Thr Gly Lys Thr Lys
            20                  25                  30

Asp Val Asn Phe Arg Leu Glu Gln Leu Lys Arg Leu Lys His Ala Ile
        35                  40                  45

Leu Asp Tyr Arg Asp Arg Ile Val Glu Ala Val Gly Ala Asp Leu Arg
    50                  55                  60

Arg Pro Glu Phe Glu Ala Tyr Phe Glu Ile Ala Ser Ile Ala Glu Val
65                  70                  75                  80

Asn Thr Ala Ile Ala Arg Leu Lys Ser Trp Ala Lys Pro Lys Arg Val
                85                  90                  95
```

```
Ser Thr Ser Leu Asp Gln Phe Pro Ser Arg Ala Arg Ile His Pro Glu
            100                 105                 110

Pro Leu Gly Val Val Leu Ile Val Ala Pro Trp Asn Tyr Pro Phe Gln
        115                 120                 125

Leu Thr Met Ser Pro Leu Val Gly Ala Ile Ala Gly Asn Cys Ala
    130                 135                 140

Val Leu Lys Pro Ser Glu Ile Ala Pro His Thr Ala Ala Val Val Ser
145                 150                 155                 160

Asp Leu Ile Arg Ser Thr Phe Pro Pro Glu Tyr Val Thr Ala Ile Glu
                165                 170                 175

Gly Gly Val Glu Thr Ser Gln Ser Leu Leu Glu Gln Lys Phe Asp Lys
            180                 185                 190

Ile Phe Phe Thr Gly Gly Thr Arg Ile Gly Gln Ile Val Met Glu Ala
        195                 200                 205

Ala Ala Lys His Leu Thr Pro Val Thr Leu Glu Leu Gly Gly Lys Ser
    210                 215                 220

Pro Cys Ile Val Asp Ala Asp Val Lys Leu Asp Val Ala Val Lys Arg
225                 230                 235                 240

Ile Val Trp Gly Lys Phe Ile Asn Ala Gly Gln Thr Cys Val Ala Pro
                245                 250                 255

Asp Tyr Leu Leu Val Asp Arg Arg Val Lys Pro Arg Leu Leu Glu Ala
            260                 265                 270

Val Arg Gln Gln Val Arg Glu Phe Phe Gly Asp Asp Pro Ala Lys Ser
        275                 280                 285

Ala Asp Phe Cys Arg Met Val Ser Asp Arg His Phe Asp Arg Val Ala
    290                 295                 300

Ser Leu Leu Glu Asn Arg Gly Asn Ala Glu Ile Val Val Gly Gly Gln
305                 310                 315                 320

Cys Asp Arg Ser Asp Arg Tyr Ile Ala Pro Thr Val Leu Asp Asn Val
                325                 330                 335

Ser Trp Asn Asp Pro Val Met Gln Asp Glu Ile Phe Gly Pro Ile Leu
            340                 345                 350

Pro Val Leu Glu Tyr Asp Ser Leu Asp Asp Ala Ile Asp Arg Val Ala
        355                 360                 365

Ser Arg Pro Lys Pro Leu Ala Leu Tyr Val Phe Ser Asn Asn Lys Pro
    370                 375                 380

Phe Gln Asn Arg Val Leu Arg Glu Thr Ser Ser Gly Gly Ala Cys Val
385                 390                 395                 400

Asn Asp Thr Val Met His Leu Ala Val Ser Asp Leu Pro Phe Gly Gly
                405                 410                 415

Val Gly Asp Ser Gly Met Gly Ser Tyr His Gly Lys Ala Ser Phe Asp
            420                 425                 430

Thr Phe Ser His Phe Lys Ser Val Leu Asn Lys Gly Leu Trp Phe Asp
        435                 440                 445

Leu Asn Trp Arg Tyr Ala Pro Tyr His Gln Trp Gln Leu Ser Leu Leu
    450                 455                 460

Lys Arg Ile Ile Gly
465

<210> SEQ ID NO 15
<211> LENGTH: 1218
<212> TYPE: DNA
<213> ORGANISM: Geitlerinema sp.

<400> SEQUENCE: 15
```

```
atgaagattc tcgtactgaa tgctggctcg agttctcaga aaagctgttt gtacgacgtt    60
cccggtgcgg ggtttcccga tacgccccaa gaaccgattt gggaagcaac catcgattgg   120
ggcgtgggga cggaatacgg actgttaact gtcgaagcca acgagacgaa gcagaaaagc   180
gaactctcga tttacgctcg ggcccacggt ttggggaaa tgctggatac gctggtgcag    240
ggcgaaacga aggttctcga ggacttgtcg gaaattgcga tcgtcggtca tcgggtggtt   300 cacggggaa cggagtattc ggacgctacg tatattacgc cagcggtgaa acaagccatt    360
gaagatttga ttcccttagc ccccaaccac aaccccgctc atttagaaga aatcctcgct   420
gtcgaggaag tgttgggaga cgtaccacaa gtggcggtat tcgataccgg gtttcacagt   480
caaatgccga catcggtggc ggcgtatccg attccctatc gctggtttga aaagggagtg   540
cgtcggtatg ggtccacgg tatcagccat cgctactgtg ccgaacgtgc ggcgaactc     600 ctcgaggagc cgttggaatc gctgcgaatc gtaacttgtc atttgggaca tggctgttct   660 ctggcggcg ttcgcgacgg aatgagtgtg aatacgacga tgggtttcac gccgttggaa    720
gggttgatga tggggagtcg tagcggttcg atcgatccgg cgattcccat gtatttgatg   780
cgcgaggaag ggtcgatttt cgagggcgtg gataagatgc tgaataagga atcgggactc   840
aaaggcgttt ctggtgagtc gggggatatg cgatcgatcc tcaaggcgat gggagagggg   900
agcgatcgcg cagagttggc gttcgagatg tacgtctctc gattgcagag tgcgatcgcc   960
tcgatgattc cccagttagg ggggttagat gttttggcat ttacggcggg tgtcggcgag   1020
aattccgccg acgtgcgagc ggcaacttgt gcggggttag atttttttggg cttaaaactc   1080 gattcgcgcc aaaacgccgc gtctcccaag gatgcggata tcgcgtcaat ggattcgacg   1140 gtgcggggtgt tggtgattcg cgctcaggag gattgggcga tcgcggggga atgttggaag   1200
ttggtaaagg taggttag                                                 1218
```

<210> SEQ ID NO 16
<211> LENGTH: 405
<212> TYPE: PRT
<213> ORGANISM: Geitlerinema sp.

<400> SEQUENCE: 16

| Met | Lys | Ile | Leu | Val | Leu | Asn | Ala | Gly | Ser | Ser | Gln | Lys | Ser | Cys |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Leu Tyr Asp Val Pro Gly Ala Gly Phe Pro Asp Thr Pro Gln Glu Pro
            20                  25                  30

Ile Trp Glu Ala Thr Ile Asp Trp Gly Val Gly Thr Glu Tyr Gly Leu
        35                  40                  45

Leu Thr Val Glu Ala Asn Glu Thr Lys Gln Lys Ser Glu Leu Ser Ile
    50                  55                  60

Tyr Ala Arg Ala His Gly Leu Gly Glu Met Leu Asp Thr Leu Val Gln
65                  70                  75                  80

Gly Glu Thr Lys Val Leu Glu Asp Leu Ser Ile Ala Ile Val Gly
                85                  90                  95

His Arg Val Val His Gly Gly Thr Glu Tyr Ser Asp Ala Thr Tyr Ile
            100                 105                 110

Thr Pro Ala Val Lys Gln Ala Ile Glu Asp Leu Ile Pro Leu Ala Pro
        115                 120                 125

Asn His Asn Pro Ala His Leu Glu Glu Ile Leu Ala Val Glu Glu Val
    130                 135                 140

Leu Gly Asp Val Pro Gln Val Ala Val Phe Asp Thr Ala Phe His Ser
145                 150                 155                 160

-continued

```
Gln Met Pro Thr Ser Val Ala Ala Tyr Pro Ile Pro Tyr Arg Trp Phe
            165                 170                 175
Glu Lys Gly Val Arg Arg Tyr Gly Phe His Gly Ile Ser His Arg Tyr
            180                 185                 190
Cys Ala Glu Arg Ala Ala Glu Leu Leu Glu Glu Pro Leu Glu Ser Leu
            195                 200                 205
Arg Ile Val Thr Cys His Leu Gly His Gly Cys Ser Leu Ala Ala Val
            210                 215                 220
Arg Asp Gly Met Ser Val Asn Thr Thr Met Gly Phe Thr Pro Leu Glu
225                 230                 235                 240
Gly Leu Met Met Gly Ser Arg Ser Gly Ser Ile Asp Pro Ala Ile Pro
                245                 250                 255
Met Tyr Leu Met Arg Glu Glu Gly Phe Asp Phe Glu Gly Val Asp Lys
                260                 265                 270
Met Leu Asn Lys Glu Ser Gly Leu Lys Gly Val Ser Gly Glu Ser Gly
            275                 280                 285
Asp Met Arg Ser Ile Leu Lys Ala Met Gly Glu Gly Ser Asp Arg Ala
        290                 295                 300
Glu Leu Ala Phe Glu Met Tyr Val Ser Arg Leu Gln Ser Ala Ile Ala
305                 310                 315                 320
Ser Met Ile Pro Gln Leu Gly Gly Leu Asp Val Leu Ala Phe Thr Ala
                325                 330                 335
Gly Val Gly Glu Asn Ser Ala Asp Val Arg Ala Ala Thr Cys Ala Gly
                340                 345                 350
Leu Asp Phe Leu Gly Leu Lys Leu Asp Ser Arg Gln Asn Ala Ala Ser
            355                 360                 365
Pro Lys Asp Ala Asp Ile Ala Ser Met Asp Ser Thr Val Arg Val Leu
            370                 375                 380
Val Ile Arg Ala Gln Glu Asp Trp Ala Ile Ala Gly Glu Cys Trp Lys
385                 390                 395                 400
Leu Val Lys Val Gly
                405
```

BIOFILM PHOTOBIOREACTOR SYSTEM AND METHOD OF USE

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

This application includes a Sequence Listing submitted electronically as a text file named "Biofilm_Photobioreactor_System.txt", created on Sep. 28, 2012, with a size of 44 KB. The sequence listing consists of 16 sequences and is incorporated by reference into the specification in its entirety.

BACKGROUND

The possibility of using algae for the production of fuel and chemicals has attracted the interest of researchers, government and business for many years. Efforts to commercialize the production of fuel from algae have brought to light problems that must be solved to make this approach practical. The present invention is a novel approach to avoid or mitigate certain problems.

Under conventional approaches to algal biofuels, algal biomass is accumulated in open ponds or photobioreactors and harvested for conversion to fuel. The composition of the biomass may be altered to some extent through manipulation of the organism genetics or of the environment in which the organism is cultured, but generally there is a trade-off between optimizing composition and maximizing accumulation of biomass.

Under an alternative approach, the genetics and environment of a photosynthetic organism are manipulated to force the flux of carbon through photosynthesis into a desired product instead of toward accumulation of biomass. In the present invention, photosynthetic organisms are cultured as a biofilm inside a photobioreactor and maintained in stationary phase, and the environmental conditions in the photobioreactor are manipulated to induce the organisms to make a biofuel product, such as ethanol.

Obligate photosynthetic organisms require $CO_2$ as a feedstock to make a product or to accumulate biomass. One problem is that, if a photosynthetic organism is cultured in a body of water in a photobioreactor or pond that is exposed to $CO_2$ contained in air, then passive diffusion of carbon from air into water across the gas/liquid interface generally is not as efficient in sustaining maximal rates of photosynthesis. Accordingly, supplemental $CO_2$ usually must be added to cultures of photosynthetic organisms that are highly productive. The use of supplemental $CO_2$ significantly increases capital costs and operating costs, thereby reducing the profitability and rate of return of $CO_2$-supplemented systems.

Limited diffusion may be ameliorated by increasing the exposure of the culture of photosynthetic organisms to air, beyond the degree of exposure found with a culture contained in a body of water. Diffusion of $CO_2$ into a culture increases as the surface area of the culture that is in contact with air increases. In addition, many organisms express carbonic anhydrase at the cell surface, which catalyzes the conversion of carbon dioxide and water to bicarbonate and protons and thereby increases the rate of diffusion of $CO_2$ from the gas phase into the liquid phase:

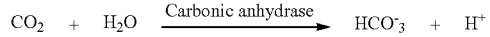

$$CO_2 + H_2O \xrightarrow{\text{Carbonic anhydrase}} HCO_3^- + H^+$$

As a result, an air-exposed culture of an appropriate organism can achieve high productivity without $CO_2$ supplementation.

In many circumstances, gas phase delivery of $CO_2$ is preferred over other delivery modes. Because the concentration of $CO_2$ in air is typically less than 0.1% by volume, sustained elevated productivity by a culture requires considerable air throughput. The present invention provides a photobioreactor with a short airflow path and sufficiently low resistance to airflow that the necessary throughput of air can be achieved without high capital or operating costs. In some circumstances, the most economical delivery of $CO_2$ may be from a concentrated source instead of from the air. In some circumstances the most economical delivery of $CO_2$ may be as a solution of bicarbonate. The present invention provides a photobioreactor compatible with all of these modes of $CO_2$ delivery.

Another problem is that highly productive photosynthetic cultures tend to accumulate oxygen, which is a product of oxygenic photosynthesis. High oxygen concentrations in the culture can reduce productivity both by competing for photosynthetically produced electrons and through the effects of oxygen toxicity.

In a conventional photobioreactor containing a liquid suspension culture, oxygen may be removed from the culture by vigorous gas sparging, but high energy costs may be involved. This consideration militates in favor of gas phase exchange a preferred method of removing excess oxygen from the culture. The present invention facilitates gas phase exchange by providing a very short diffusion path for oxygen removal from the culture to the air stream.

Another problem is that an organism that channels photosynthetic energy primarily into making a fuel or chemical product, instead of accumulating biomass, severely disadvantaged compared to a competing organism that does not make the fuel product, and instead channels photosynthetic energy toward growth. This disparity reduces the stability of a culture of organisms that make a fuel product, since the culture may be invaded and outcompeted by other species that do not make the fuel product. Also, the organism will undergo mutations that reduce the tendency to make the fuel product, thereby conferring a selective advantage over the productive, non-mutant type. As a result, the non-productive mutants will take over the culture, reducing or eliminating the productive organisms. This problem can be mitigated if production of the fuel or chemical product is beneficial to the organism.

If the organism makes the fuel product through fermentation, then production of the fuel product is necessary for the metabolism of the organism under anaerobic conditions and consequently the culture is more stable against mutation of the organism or invasion by non-fermenting species. The present invention facilitates fermentation to make a fuel product.

Product stability can be problematic if the fuel or chemical product is present in the culture and oxygen is present in the culture. The growth of aerobic heterotrophic bacteria that consume the product and that are present in the culture as contaminants is enabled by the availability of both oxygen and the product.

To address this problem, conventional photobioreactor or pond cultures must either incorporate unbreachable sterility barriers or must use antibiotics or other means so they are tolerant of some degree of contamination. The present invention minimizes the effect of contamination by heterotrophs on product stability and net productivity by substantially removing the product so that it is not present when oxygen is present in the culture.

Toxic effects of products such as ethanol on the organism of interest may also present problems. While product toxicity increases with productivity and product concentration, product toxicity can be mitigated by limiting the duration of exposure of the organism to the maximum product concentration. Further, exposure of the culture to product can be limited to the fermentation period, which may be conducted in darkness, in order to avoid toxicity responses that result from an interaction with photosynthetic processes.

Product purification costs are usually sensitive to concentration of the product that is extracted from a culture in a photobioreactor. It is desirable for fermentation to occur in a small fluid volume that yields elevated product concentration. The present invention provides a photobioreactor in which the fermentation volume is very small.

Capital costs must be kept within reasonable bounds for a fuel production system or method to be economically feasible. Materials, construction methods and supporting infrastructure must be chosen or designed with low cost in mind. A system of the present invention can have low material costs and a simplified infrastructure, and may be made using simple construction methods suitable for mass production. A system of the present invention may be light weight, minimizing mounting costs.

Because photosynthetic organisms in photobioreactors require exposure to sunlight, the culture in a photobioreactor may be exposed to high temperatures that are inimical to culture health and productivity. The present invention allows the management of culture temperature at low cost.

The considerations outlined above illustrate that the productivity of organisms that are cultured in a photobioreactor to make biofuel through metabolic processes may be restricted severely by limitations on uptake of $CO_2$ by the culture, removal of oxygen from the culture, genetic stability of the culture, stability of the product made by the culture, toxicity effects of the product on the culture and temperature effects on the culture.

US 2009/0181434 A1 to Aikens et al. discloses transgenic bacteria engineered to accumulate carbohydrates and a photobioreactor for cultivating photosynthetic microorganisms comprising a non-gelatinous, solid cultivation support suitable for providing nutrients and moisture to photosynthetic microorganisms and a physical barrier covering at least a portion of the surface of the cultivation support.

Aikens does not provide for the possibility of anoxic fermentation in the reactor structure or mode of operation. The photobioreactor proposed by Aikens is very different in detail from the present invention, using a different medium delivery system, a different product harvest system, and a completely different mode of operation. It does have in common with the present invention the use of a photosynthetic biofilm. The advantages of the present invention are that (1) periodic immersion provides a much more reliable uniform hydration than water seeping or dripping from a header; (2) the complexity and cost of a reactor design of the present invention are much lower; and (3) a reactor design of the present invention design lends itself to easily establishing conditions suitable for fermentation.

US 2008/0160591 A1 to Wilson at al. discloses a photobioreactor system for production of photosynthetic microorganisms that includes the use of extended surface area and an external water basin. Wilson et al. is related to the present invention in that Wilson at al. teaches the use of plastic film and similar construction techniques to produce a pattern of heat sealed welds between opposite panels. This reflects the concern of Wilson at al. with reactor cost, which is a concern also addressed by the present invention. Wilson et al. provides a photobioreactor design that is suited for the cultivation of organisms suspended in water medium. Wilson at al. is not suitable for cultivation of a photosynthetic biofilm, and hence it does not provide the separation of retained biomass from a secreted or soluble product, and it is not suitable for operation with an autofermentation cycle.

US 20090258404 A1 to Mikkelsen at al. discloses production of fermentation products such as ethanol and lactic acid in biofilm reactors by microorganisms immobilized on sterilized granular sludge. Mikkelsen et al. is similar to the present invention in that Mikkelsen at al. uses a biofilm and anoxic fermentation. The apparatus and method of Mikkelsen at al. are not suitable for a photosynthetic biofilm or for an alternation of photosynthesis and autofermentation conditions essential to the present invention.

U.S. Pat. No. 5,595,893 to Pometto at al. discloses a solid support made of a synthetic polymer for immobilization of microorganism cells to form a biofilm reactor or use in fermentation, in streams for bioremediation of contaminants, and in waste treatment systems. It is possible that the support specified by Pometto et al, would be useful in a photobioreactor of the present invention. The reactor design used by Pometto et al. and the method of use are not compatible with a photosynthetic biofilm and an alternation of photosynthesis and autofermentation conditions essential to the present invention.

These references do not teach an optimized biofilm photobioreactor system of the present invention that resolves the limitations discussed above.

SUMMARY

An object of the present invention is a photobioreactor system that supports environmental conditions in which suitable organisms form biofilms on support substrates inside the photobioreactor, make metabolic intermediate compounds through photosynthesis and convert the metabolic intermediates into chemical products such as biofuels or feedstocks through autofermentation. According to the present invention, the design of the photobioreactor system enables increased uptake of carbon dioxide by the biofilm, increased removal of oxygen improved genetic stability of the biofilm and improved stability of the chemical product, while mitigating toxicity effects of the chemical product on the biofilm and temperature effects on the biofilm. Further according to the present invention, the photobioreactor system advantageously maintains a low cost basis.

A biofilm photobioreactor system of the present invention comprises flexible film that defines a photobioreactor enclosure. The photobioreactor enclosure has a flat panel shape and at least one portion of the flexible film is translucent.

Channels defined by at least one partition are disposed in the photobioreactor enclosure. The channels are in fluid communication.

A suitable photosynthetic, autofermentative microorganism is cultured to form a biofilm in the photobioreactor enclosure. The suitable microorganism makes one or more metabolic intermediate compounds during a photosynthesis phase and converts the metabolic intermediate compound(s) to chemical product(s) during an autofermentation phase The suitable microorganism forms a biofilm on a support substrate. The support substrate is disposed in the channels and is fixed to the flexible film, the at least one partition forming the channels or a combination of both.

The photobioreactor enclosure of the biofilm photobioreactor system incorporates at least one port formed in the flexible film for adding and removing liquid and adding gas to the photobioreactor enclosure, and at least one gas exhaust vent formed in the flexible film.

A gas comprising carbon dioxide flows through the photobioreactor enclosure intermittently and contacts the biofilm during the photosynthesis phase. The gas enters the photobioreactor enclosure through the at least one port and leaves the photobioreactor enclosure through the gas exhaust vent.

A first liquid at least partially fills the photobioreactor enclosure intermittently and contacts the biofilm during the photosynthesis phase. The first liquid enters the photobioreactor enclosure and leaves the photobioreactor enclosure through the port.

A second liquid at least partially fills the photobioreactor enclosure and contacts the biofilm during the autofermentation phase. The second liquid enters the photobioreactor enclosure and leaves the photobioreactor enclosure through the port. The chemical product made by the biofilm during the autofermentation phase enters the second liquid A further object of the present invention is a method of making a biofuel through providing carbon dioxide and light to a biofilm of a suitable organism that is cultured in a photobioreactor of the present invention, such that the biofilm makes a metabolic intermediate compound through photosynthesis, and then removing light and electron acceptors such as oxygen, such that the biofilm converts the metabolic intermediate compound into a chemical product through autofermentation.

In a method of the present invention, a biofilm comprising a suitable photosynthetic, autofermentative microorganism is exposed to light. The biofilm is disposed on a support substrate that is disposed in channels of a biofilm photobioreactor and is fixed to inner surfaces of the biofilm photobioreactor.

The channels of the biofilm photobioreactor are at least partially filled alternately with a flow of gas comprising carbon dioxide and with a first liquid. The gas and the first liquid contact the biofilm and the suitable microorganism snakes a metabolic intermediate compound from light and carbon dioxide by photosynthesis.

The biofilm is deprived of light and the channels of the biofilm photobioreactor are at least partially filled with a second liquid, which contacts the biofilm and expels the gas from the biofilm photobioreactor through outlets. The suitable microorganism converts the metabolic intermediate compound(s) into chemical product(s) by autofermentation, and the chemical product(s) enters the second liquid. The second liquid containing the chemical product(s) may be extracted from the biofilm photobioreactor.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE SEVERAL VIEWS OF THE DRAWING

Embodiments of the invention will be described below with reference to the following figures.

DETAILED DESCRIPTION

Figure 1:
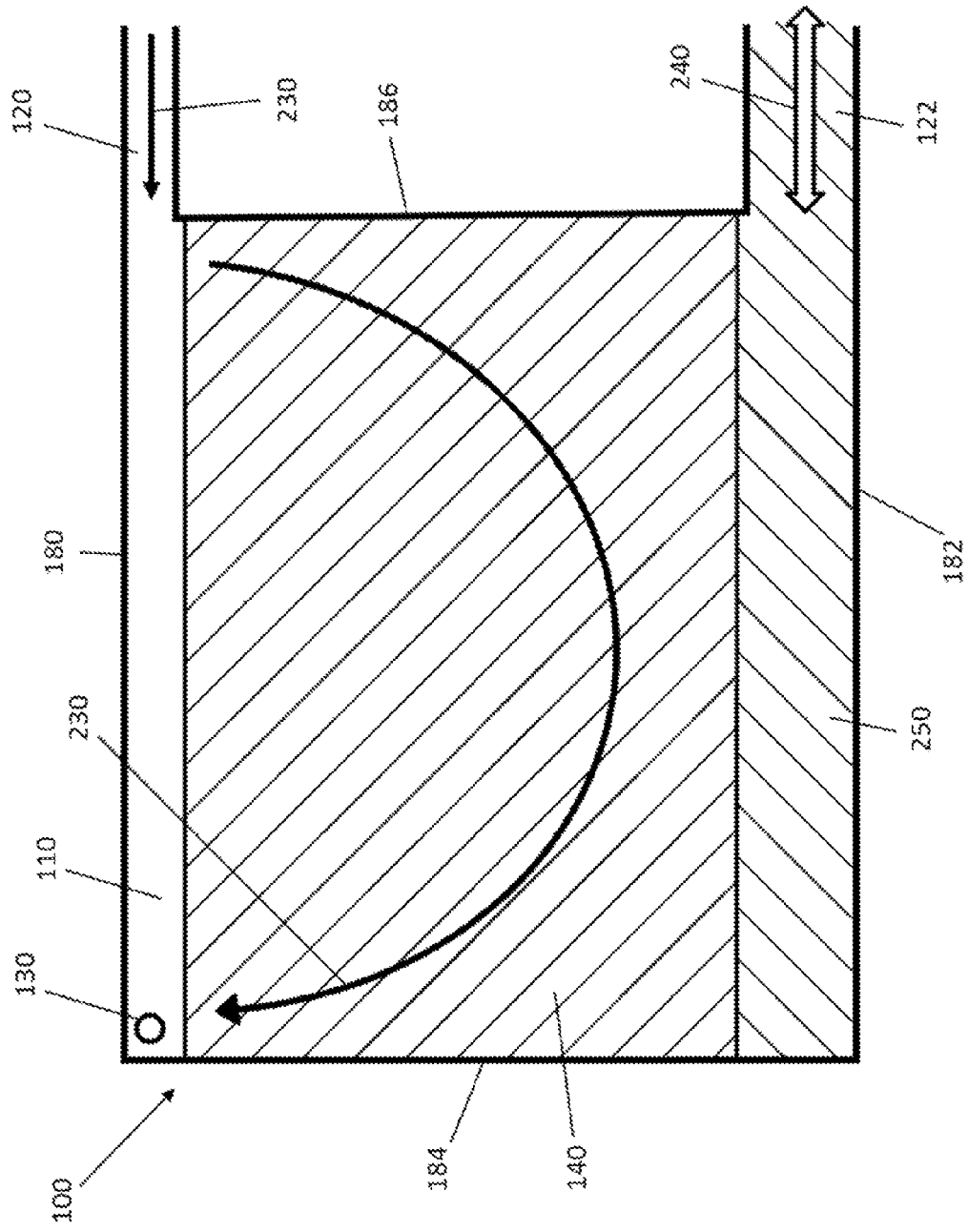
FIG. 1 shows a plan view of a flat panel biofilm photobioreactor design.

The present invention relates to biofilm photobioreactor systems and a method for using a biofilm-forming microorganism in a photobioreactor of the present invention to make metabolic intermediate(s) through photosynthesis and convert the metabolic intermediates) into chemical product(s) through autofermentation. The primary chemical product preferably is a biofuel, such as ethanol, hydrogen, propanol or butanol, or a chemical feedstock such as acetate, lactate or formate.

As used herein, the term "suitable organism" means a microorganism that is able to attach to and form a biofilm on a surface and also to make metabolic intermediate compounds through photosynthesis and chemical products such as biofuels or feedstocks through fermentation. Non-limiting examples of suitable organisms within the meaning of the present invention are *Geitlerinema, Lyngbya, Chroococcidiopsis, Calothrix, Cyanothece, Oscillatoria, Gloeothece, Microcoleus, Microcystis, Nostoc, Anabaena* and *Spirulina* species. One of ordinary skill in the art will recognize that other suitable organisms are within the scope of the present invention.

For commercial production of chemical products, it is preferable to use a suitable organism that produces only a single product. While such organisms are known, generally a mix of products is produced. It is possible, using classical genetics or genetic engineering techniques, to eliminate pathways that lead to undesired chemical products, thereby leaving only a pathway that leads to the desired chemical product. If the suitable organism does not produce the desired chemical product, the required genes can be introduced using genetic engineering techniques. It is possible in principal to begin with an organism that does not perform autofermentation and introduce the necessary genes to confer the ability to autoferment. The development of enhanced organisms is not essential to the utility of this invention, but the development of such organisms will clearly greatly enhance the commercial value of this invention.

As used herein, the term "biofilm" means an aggregate of suitable organisms in which cells adhere to each other on or within a surface, frequently embedded within a self-produced matrix of exopolysaccharide or extracellular polymeric substance (EPS). Formation of a natural biofilm begins with free-floating microorganisms attaching to a surface through real, reversible adhesion via van der Waals forces, followed by anchoring themselves sing cell adhesion structures such as pili. Biofilms are often found on solid substrates submerged in or exposed to an aqueous solution. Artificial biofilms can also be made, using a flocculating agent such as sodium silicate, or an immobilizing agent such as alginate.

As used herein, the terms "exopolysaccharide" and "extracellular polymeric substance" mean a polymeric conglomeration generally composed of extracellular polysaccharides and proteins that hold together and protect a biofilm in matrix form.

As used herein, the term "oxic" means a concentration of dissolved oxygen in water greater than about 30% saturation.

As used herein, the term "hypoxia" means a concentration of dissolved oxygen in water in the range of from about 1% to about 30% saturation.

As used herein, the term "anoxia" means a concentration of dissolved oxygen in water less than about 1% saturation.

As used herein, the term "anaerobic" refers to cellular metabolism in which oxygen is not used as an electron acceptor.

As used herein, the term "fermentation" means the process of extracting energy from metabolic intermediate compounds that are organic compounds, such as carbohydrates or osmoprotectants, under hypoxic or anoxic conditions without the use of a terminal electron acceptor such as oxygen, sulfate or nitrate. Fermentative microorganisms typically hydrolyze complex organic polymers (e.g., glycogen) to monomers (e.g., glucose), which are further converted to lower molecular weight organic acids and alcohols. For example, fermentation may include the process of glycolysis, in which glucose is metabolically converted into pyruvate, followed by conversion of pyruvate into ethanol. The concentration of oxygen or another electron acceptor below which a suitable organism will begin fermenting depends on the metabolic profile of the particular organism.

As used herein, the term "dark fermentation" means the fermentation of metabolic intermediate compounds such as organic substrates to hydrogen in the absence of light.

As used herein, the term "autofermentation" means that metabolic intermediate compounds that are made anabolically by the cells during photosynthesis and stored internally are catabolized under hypoxic or anoxic conditions to yield energy that may be used by the cell. Without using supplemental organic compounds, autofermenting cells produce carbon dioxide, chemical products such as biofuels and feedstocks, and energy used to regenerate adenosine triphosphate.

Photobioreactors and methods in accordance with the present invention are useful for producing a wide range of chemical products including acids, alcohols, ketones and hydrogen, and more specifically chemical products such as ethanol, butanol, propanol, methanol, propanediol, butanediol, lactate, proprionate, acetate, succinate, butyrate, formate and acetone.

As used herein, the term "metabolic intermediate compound" means an organic compound made by a microorganism through photosynthesis. Non-limiting examples of metabolic intermediate compounds are carbohydrates and osmoprotectants.

As used herein, the term "carbohydrate" means an organic compound that consists only of carbon, hydrogen, and oxygen. Non-limiting examples of carbohydrates are glycogen and glucose.

As used herein, the term "osmoprotectant" means a small molecule that acts as an osmolyte and helps organisms survive osmotic stress. Non-limiting examples of osmoprotectants are trehalose and glucosyl-glycerol.

As used herein, the term "osmolyte" means a compound that plays a rode in maintaining fluid balance and volume of a microorganism cell.

As used herein, the term "chemical product" means an organic compound made by a microorganism through fermentation or autofermentation. Non-limiting examples of chemical products are biofuels and feedstocks.

As used herein, the term "biofuel" means a type of fuel that derives energy from biological carbon fixation. Biofuels include fuels derived from biomass conversion or from cell metabolism, as well as solid biomass, liquid fuels and various biogases. Biologically produced alcohols such as ethanol may be produced by the action of microorganisms and enzymes through the fermentation of sugars or starches. Non-limiting examples of biofuels are ethanol, hydrogen, propanol and butanol.

As used herein, the term "feedstock" means a chemical compound that can be used as the starting material to make other products of interest, where such products are made using means other than the biofilm photobioreactor of the present invention. Non-limiting examples of feedstocks are acetate, lactate and formate.

As used herein, the term "biofilm photobioreactor" means a device or system used to support a biologically active environment for the cultivation of photosynthetic, autofermentative microorganisms. The biofilm photobioreactor may be constructed of flexible film that may be translucent. A biofilm photobioreactor of the present invention may be semi-closed against the exchange of gases and contaminants with the outside environment while permitting penetration of light through walls of the biofilm photobioreactor, or otherwise incorporating a light source, to provide photonic energy input for the photosynthetic culture of microorganisms contained in the biofilm photobioreactor. Cells of the photosynthetic microorganism are immobilized in layers on a support substrate inside the biofilm photobioreactor and the cell layers accumulate over time, forming a biofilm.

As used herein, the term "flexible film" means a thin continuous polymeric material or coating. Non-limiting examples of materials that can be used in flexible films suitable for use with the present invention are polyolefins, polyesters and vinyl copolymers thereof.

As used herein, the term 'translucent' means allowing light to pass through, with or without scattering of photons.

As used herein, the term "support substrate" means a surface upon which a suitable organism is able to adhere and form a biofilm, Non-limiting examples of substrates within the meaning of the present invention that may be used with suitable organisms to form biofilms are films, filters, fabrics, foams and felts of polyesters, polyolefins, polyurethanes, polyamides, polyimides, polycarbonates, polydienes and polyacrylics adhered to the plastic film of the photobioreactor. One of ordinary skill in the art will recognize that the use of other substrates is contemplated within the scope of the present invention.

As used herein, the term "sparging" means a process whereby a chemically inert gas is bubbled through a liquid.

As used herein, the term "electron acceptor" means a chemical entity that accepts electrons transferred to it from another compound. An electron acceptor is an oxidizing agent that by virtue of its accepting electrons, is itself reduced in the process. An electron acceptor can, be a chemical entity such as ferric iron, sulphate, nitrate or nitrite, for example. A terminal electron acceptor is a co pound such as oxygen, that receives or accepts an electron during cellular respiration.

As used herein, the term "substantially depleted of electron acceptors" describes an environment in which the partial pressures of oxygen, nitrate, sulphate, ferric iron, nitrite and other electron acceptors are love enough to facilitate anaerobic metabolism.

As used herein, the term "medium" means a liquid or gel designed to support the growth of microorganisms.

As used herein, the term "BG-11" means a standard cultivation medium for cyanobacteria that is well known to those of skill in the art. BG-11 contains all of the nutrients required for growth of many species of cyanobacteria. BG-11 is sold by, for example, Sigma-Aldrich Co LLC as the product "Cyanobacteria BG-11 Freshwater Solution" under SKU C3061.

The term "about" is used herein to mean approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) by a variance of 20%.

Figure 2:
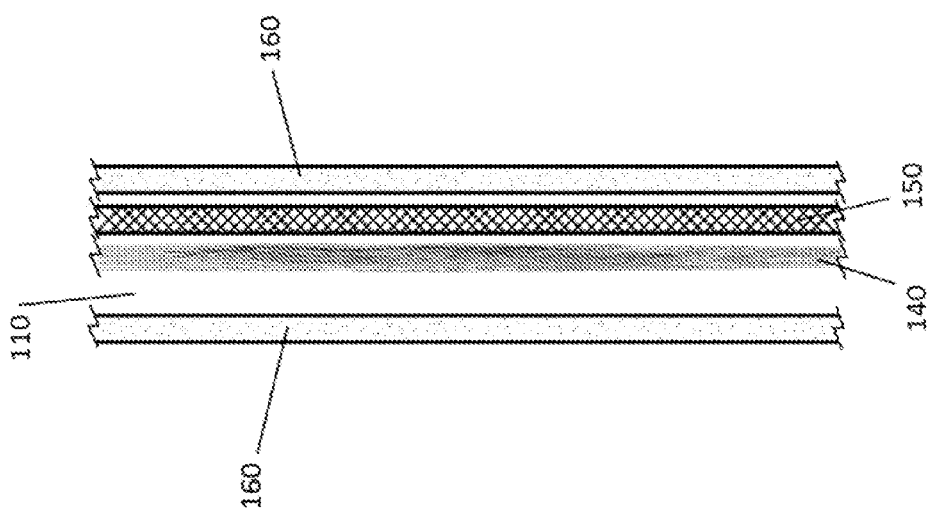
FIG. 2 shows a side sectional view of a flat panel biofilm photobioreactor design.

FIGS. 1 and 2 show an embodiment of a biofilm photobioreactor 100 configured as a flat panel photobioreactor enclosure 110 with an internal void volume. The photobioreactor enclose 110 is oriented more or less vertically, with a port 120 for inlet of gas flow 230 and a port 122 for inlet and outlet of liquid flow 240, and an exhaust vent 130 for gas flow 230. Gas flow 230 and liquid flow 240 through the inlet and outlet ports 120 and 122 may be controlled by valves, pumps 330, fans 190 or other suitable devices. The exhaust vent 130 for gas flow 230 may be passive, such that gas flow 230 inside the photobioreactor enclosure 110 is forced through the exhaust vent 130 by the pressure head inside the photobioreactor enclosure 110.

Figure 8:
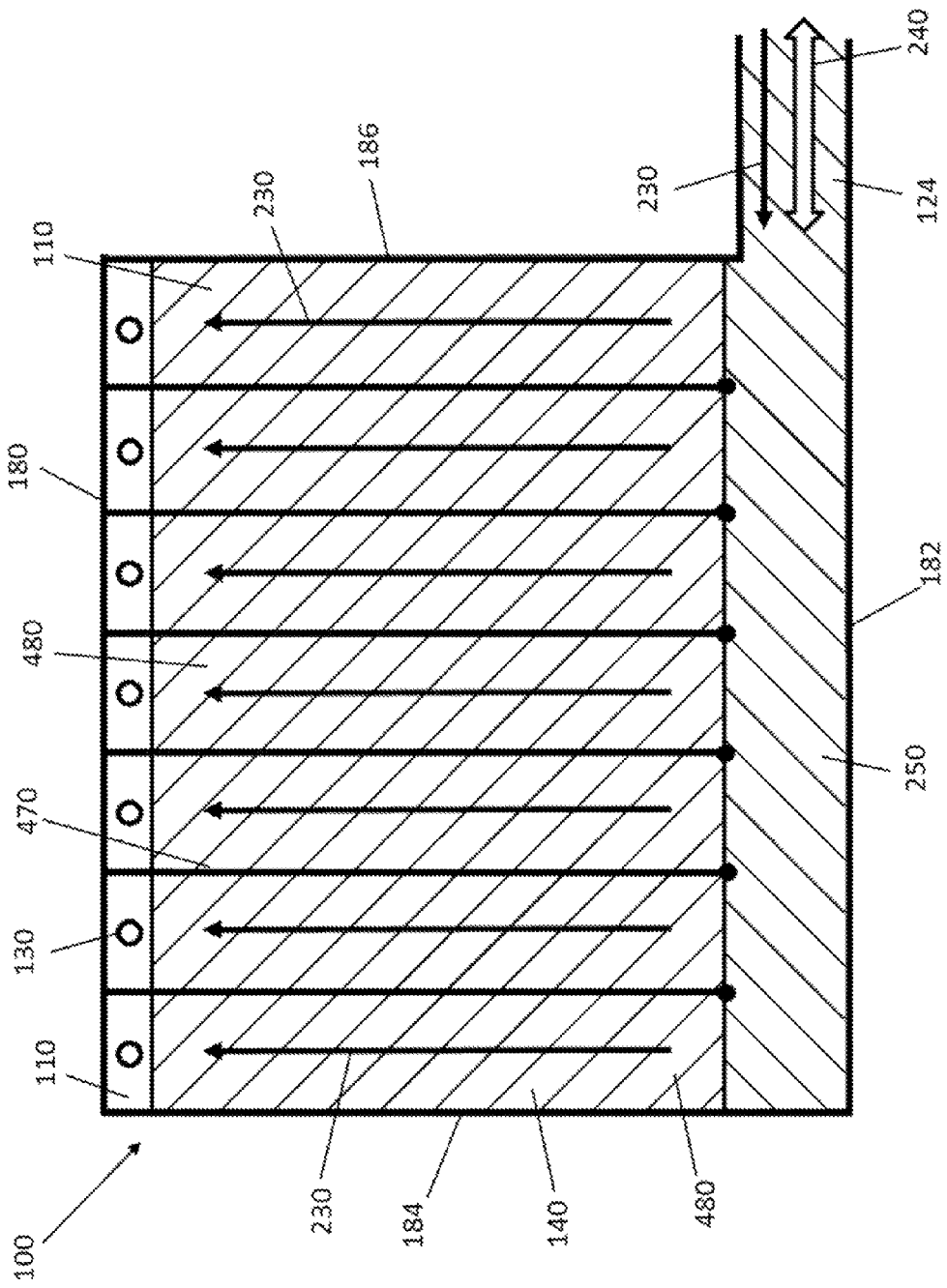
FIG. 8 shows a plan view of a flat panel biofilm photobioreactor design with multiple channels for flow of air and water.

Positioning the inlet port 120 for gas flow 230 and the exhaust vents 130 near the top edge 180 of the photobioreactor enclosure 110 eliminates the need to use valves or other potentially costly devices that would be required to prevent liquid flow 240 out of the photobioreactor enclosure 110 through ports 120 positioned lower on the photobioreactor enclosure 110. Alternatively, the inlet port 120 for gas flow 230 can be positioned near the bottom edge 182 of the photobioreactor enclosure 110, with external protection against backflow. If desired, the photobioreactor enclosure 110 can have a single port 124 for both gas flow 230 and liquid flow 240, as shown in FIG. 8.

The biofilm photobioreactor 100 may be inoculated with a suitable organism that forms a biofilm 140 on a support substrate 150 inside the photobioreactor enclosure 110. The support substrate 150 may be fixed in place by adhering the support substrate 150 to at least one wall 160 or edge 180 of the photobioreactor enclosure 110. In some embodiments, one or more pieces of support substrate 154 extend vertically and horizontally between the edges 180 of the internal void volume of the photobioreactor enclosure 110. As depicted in FIGS. 1 and 2, the support substrate 150 lies underneath, and is covered by, the biofilm 140 growth.

In preferred embodiments, the photobioreactor enclosure 110 is made from flexible film. Exemplary properties of a suitable flexible film for use it the present invention are translucency, tolerance to UV radiation, low oxygen diffusivity, low cost, light weight and acceptable durability. Flexible film edges 180 are bonded together, preferably through heat sealing, to form the photobioreactor enclosure 110.

At least one flexible film wall 160 of the photobioreactor enclosure 110 is translucent so that the biofilm 140 on the support substrate 150 contained within the photobioreactor enclosure 110 may be exposed to light from the sun or another source that provides photosynthetically active radiation having wavelengths from 400 to 700 nanometers. If only one flexible film wall 160 of the photobioreactor enclosure 110 is translucent, then the support substrate 150 preferably is adhered to the non-translucent wall 160. Suitable organisms in the biofilm 140 utilize the light to make metabolic intermediate compounds through photosynthesis.

Figure 3:
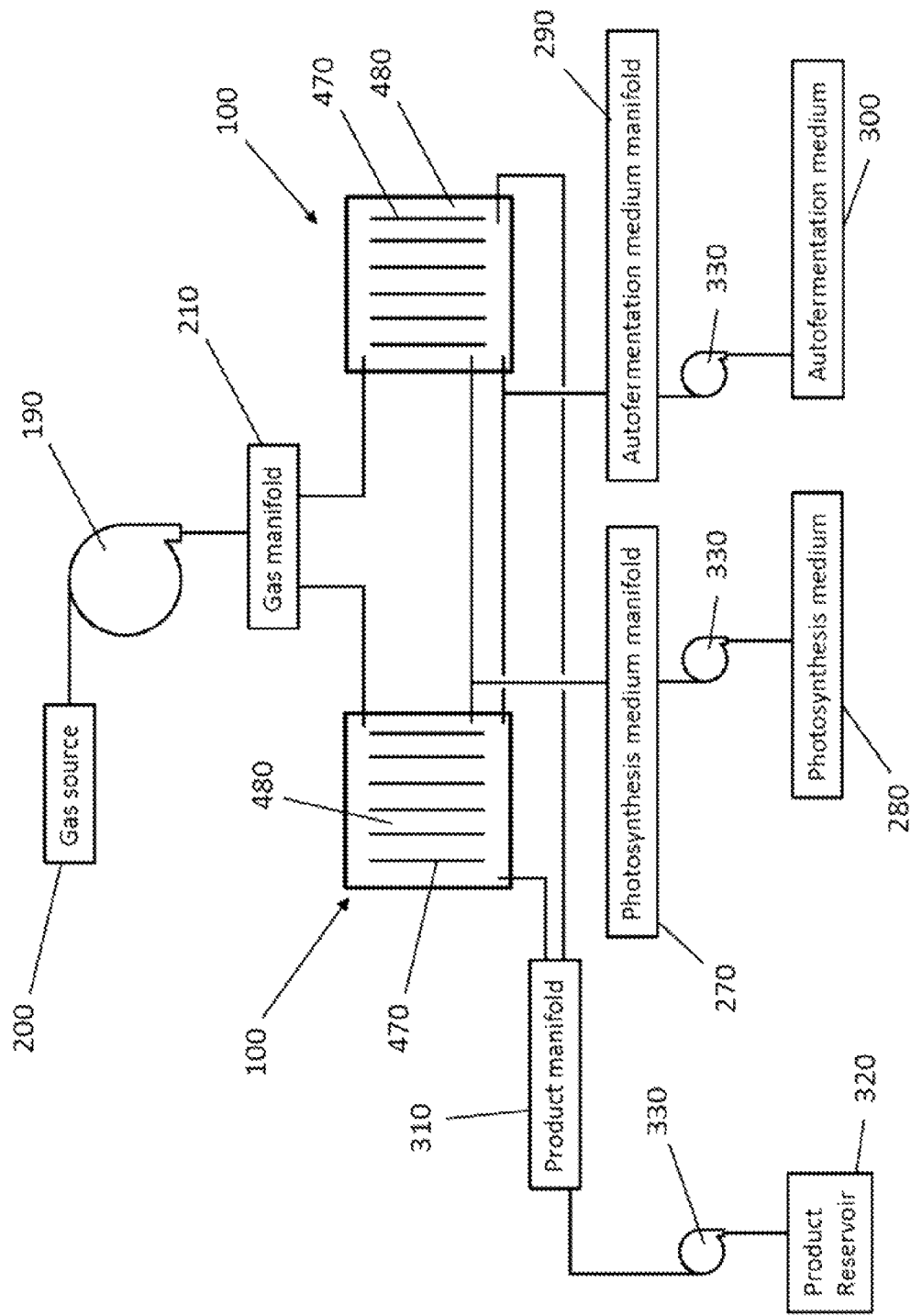
FIG. 3 shows a schematic diagram of a flat panel biofilm photobioreactor with gas and media supply.
Figure 4:
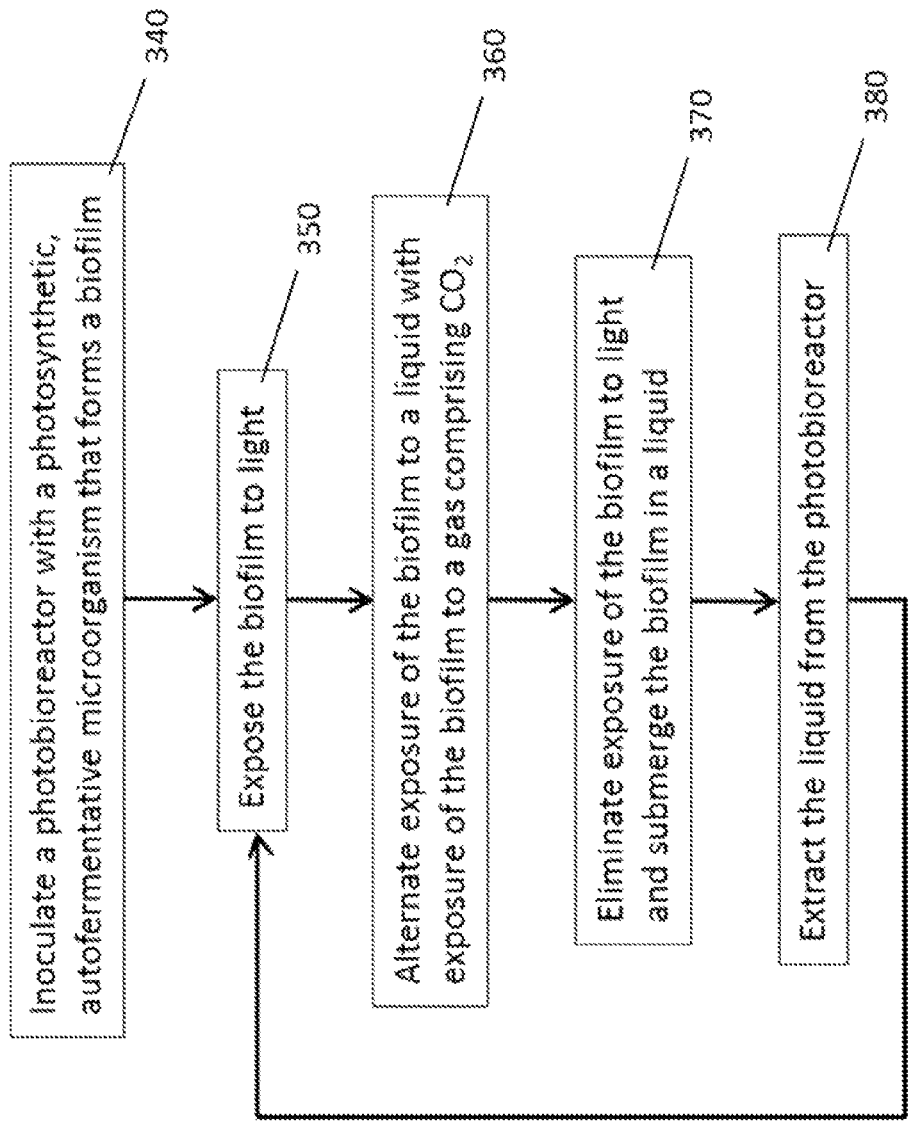
FIG. 4 shows a block diagram of steps of operating a flat panel biofilm photobioreactor.
Figure 5:
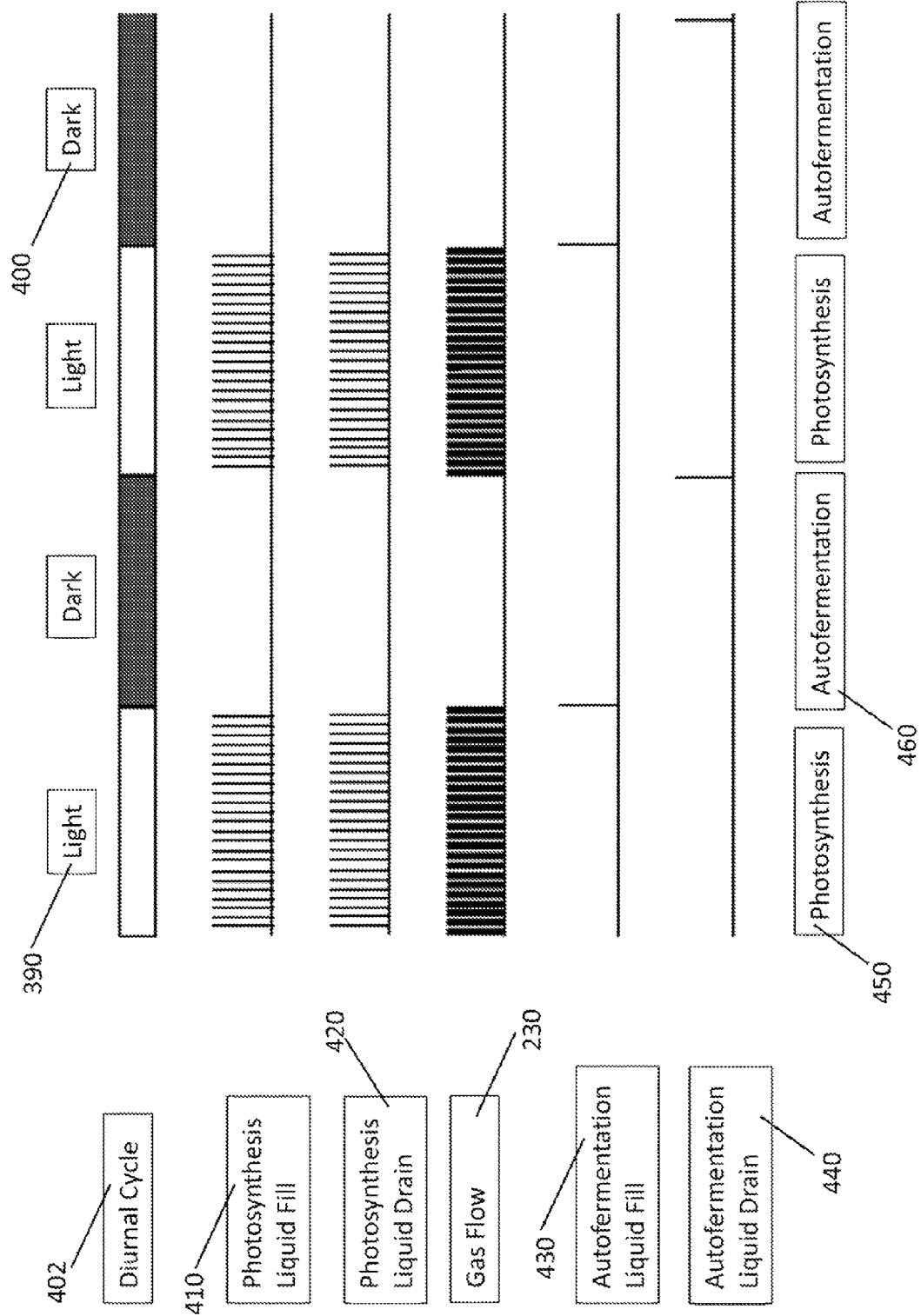
FIG. 5 shows a frequency diagram of steps of operating a flat panel biofilm photobioreactor.

Operation of a biofilm photobioreactor 100 of the present invention may be understood with further reference to FIGS. 3, 4 and 5. The biofilm photobioreactor 100 is inoculated 340 with a suitable organism that forms a biofilm 140. Internal environmental conditions are established that allow the biofilm 140 to first conduct photosynthesis, then autofermentation.

To initiate a photosynthesis period 450, the biofilm 140 is exposed 350 to light, and carbon is supplied to the suitable organisms by contacting 360 a gas, such as air, comprising carbon dioxide with the biofilm 140. Gas flow 230 to the photobioreactor enclosure 110 can be supplemented with carbon dioxide, but preferably will be air that is not supplemented. Suitable organisms in the biofilm 140 utilize the carbon dioxide to make a metabolic intermediate compound through photosynthesis. The metabolic intermediate compound is stored in the biofilm 140.

Gas flow 230 through the photobioreactor enclosure 110 can be created by using, for example, a fan 190. Gas flow 230 enters the photobioreactor enclosure 110 through a port 120 and leaves the photobioreactor enclosure 110 through the exhaust vents 130. In some embodiments, gas flow 230 from a gas source 200 is moved to a gas manifold 210, which splits the gas flow 230 among multiple biofilm photobioreactors 100 configured in an array 220. One of skill in the art will appreciate that gas and liquid flows among the components shown in FIG. 3 can be established using tubing, hoses or other means comprising any materials suitable for accommodating gas and liquid flows.

The biofilm 140 will tend to become dehydrated as a result of exposure to gas flow 230 that contains less than 100% relative humidity, and as a result of exposure to light, which raises the temperature in the photobioreactor enclosure 110. Dehydration of the biofilm 140 will result in reduced productivity, so water, culture medium another suitable liquid 250 is added 360 periodically to the photobioreactor enclosure 110 to immerse and hydrate the biofilm 140. In some embodiments, the liquid 250 is a freshwater medium. The photobioreactor enclosure 110 is filled with the liquid 250 to a level below the exhaust vents 130, which expels gas flow 230 from the photobioreactor enclosure 110.

During the photosynthesis period 450, gas flow 230 through the photobioreactor enclosure 110 is periodically alternated with liquid flow 240 that fills the photobioreactor enclosure 110 at least partially. In some embodiments, the liquid 250 is a photosynthesis medium 280 that is split by a manifold 270 among multiple biofilm photobioreactors 100 configured in an array 220.

The optimal time periods of gas flow 230 and liquid flow 240 can be determined experimentally by monitoring carbon dioxide concentration in the gas flow 230 exiting the photobioreactor enclosure 110 through the exhaust vents 130, which indicates the rate of consumption of carbon dioxide and the rate of productivity by the biofilm 140. Generally, liquid flow 240 to immerse the biofilm 140 should occur frequently enough to maintain a relatively constant rate of carbon dioxide consumption by the biofilm 140.

In some embodiments, each period of gas flow 230 continues for any length of time in the range of from about five minutes to about four hours. In some embodiments, the photobioreactor enclosure 110 is quickly filled with liquid 250 and then drained, with the total period of liquid flow 240 to fill and drain the photobioreactor enclosure 110 taking about 10 seconds. In some embodiments, the total period of liquid flow 240 continues for about 20 minutes, or for any period in the range of from about 10 seconds to about 20 minutes.

The photosynthesis period 450 may continue for the length of diurnal sunlight, or otherwise for any length of time that is sufficient for the biofilm 140 to make and accumulate metabolic intermediate compound(s). Subsequently, an autofermentation period 460 is initiated in order to force the biofilm 140 to convert the metabolic intermediate compound(s) into chemical product(s) through autofermentation.

The autofermentation period 460 may continue for the length of diurnal darkness, or otherwise for any length of time that is sufficient for the biofilm 140 to convert the accumulated metabolic intermediate compound(s) into chemical product(s). A highly active biofilm 140 may convert accumulated metabolic intermediate compound(s) in a shorter period of time. In some embodiments, the autofermentation period 460 continues for any period of time in the range of from about one hour to about 18 hours.

To induce an autofermentation period 460, the biofilm 140 is deprived 370 of light, and the photobioreactor enclosure 110 is at least partially filled 370 with liquid 250 to exclude gas flow 230 from the photobioreactor enclosure 110 and deprive the biofilm 140 of terminal electron acceptors such as oxygen. The suitable organisms that comprise the biofilm 140 produce oxygen when exposed to light, and the initiation of n autofermentation period 460 is hindered when the biofilm 140 is producing oxygen. Accordingly, depriving 370 the biofilm 140 of exposure to light facilitates the initiation of an autofermentation period 460.

In some embodiments, the liquid 250 is a fermentation medium 300 that is split by a manifold 290 among multiple biofilm photobioreactors 100 configured in an array 220.

The liquid 250 remains in the photobioreactor enclosure 110 for the duration of the autofermentation period 460. Gas flow 230 through the photobioreactor enclosure 110 during the photosynthesis period 450 is expelled through the exhaust vents 130 when the photobioreactor enclosure 110 is filled with the liquid 250 at the beginning of the autofermentation period.

FIG. 5 further exemplifies the sequence and relative duration of events in the operation of the biofilm photo bioreactor 100. Time increases from left to right along the horizontal scale. Light periods 390 and dark periods 400 of the diurnal cycle 402 are color-coded. The occurrence of "Photosynthesis Liquid Fill" 410, "Photosynthesis Liquid Drain" 420, "Gas Flow" 230, "Autofermentation Liquid Fill" 430, and "Autofermentation Liquid Drain" 440 are indicated by the placement of vertical lines or bars, with the height of each line or bar indicating the velocity of gas flow 230 or liquid flow 240 and the width of each line or bar indicating the duration of non-zero flow velocity. The opposition of "Photosynthesis Liquid Fill" 410 with "Photosynthesis Liquid Drain" 420, and "Autofermentation Liquid Fill" 430 with "Autofermentation Liquid Drain" 440 additionally indicate directionality of non-zero flow velocity. FIG. 5 accordingly shows that photosynthesis 450 occurs in the biofilm 140 during light periods 390, during which there are periods of gas flow 230 through the photobioreactor enclosure 110 alternating with shorter periods of liquid flow 240 filling and then draining the photobioreactor enclosure 110. The photobioreactor enclosure 110 is filled with liquid 250 for the duration of the dark periods 400, during which autofermentation 460 occurs.

After an autofermentation period 460 ends, the liquid 250 containing chemical product(s) may be removed 380 from the photobioreactor enclosure 110 and processed using suitable means known to one of skill in the art to extract chemical product(s) from the liquid. In some embodiments, liquid 250 containing chemical product(s) from multiple biofilm photobioreactors 100 configured in an array 220 is combined by a product manifold 310 and stored in a product reservoir 320. It is desirable to remove and store the liquid containing the chemical product(s) under anaerobic conditions in order to suppress the growth of heterotrophic microorganisms that may consume chemical product(s) and reduce yield.

The liquid 250 used to fill the photobioreactor enclosure 110 during the autofermentation period 460 may be a freshwater medium that is substantially depleted of terminal electron acceptors before it is added to the photobioreactor enclosure 110. In some embodiments, the medium used during an autofermentation period 460 contains a dissolved oxygen concentration of less than about 15% saturation.

When an autofermentation medium 300 is prepared, the concentration of dissolved oxygen may be reduced by sparging the autofermentation medium 300 with a gas such as nitrogen or by vacuum degasing the autofermentation medium 300, for example. The autofermentation medium 300 is preferably stored outside the photobioreactor enclosure 110 under anoxic conditions in order to prevent the absorption of oxygen.

As an alternative to using sparging or other pre-treatments, the concentration of dissolved oxygen and other terminal electron acceptors in the autofermentation medium 300 may be reduced by adding the autofermentation medium 300 to the photobioreactor enclosure 110 and using the biofilm 140 to consume residual or ambient oxygen and other terminal electron acceptors through respiration. The time required for the respiratory activity of the biofilm 140 to create hypoxic or anoxic conditions that are suitable for autofermentation will be determined by factors such as the respiratory rate of the biofilm 140 the volume of autofermentation medium 300 and the initial concentrations of oxygen and other electron acceptors in the autofermentation medium 300.

One of skill in the art will appreciate that the biofilm photobioreactor 100 can be appropriately designed by sizing the photobioreactor enclosure 110 and selecting the biofilm 140 organism and autofermentation medium 300 such that the biofilm 140 will consume residual or ambient oxygen and other terminal electron acceptors and begin an autofermentation period 460 within a practical time period. In some embodiments, creation of autofermentation conditions and conversion of accumulated metabolic intermediate compound(s) to the chemical product(s) may be accomplished by the biofilm photobioreactor 100 in about one hour.

It may also be desirable to minimize the concentration of terminal electron acceptors present in the liquid 250 that is used to moisten the biofilm 140 during the photosynthesis period 450. This treatment may help increase the efficiency and speed of the transition from photosynthesis period 450 to autofermentation period 460 by reducing the quantity of terminal electron acceptors that carries over from the photosynthesis period 450 to the autofermentation period 460. The optimal concentration of terminal acceptors in the liquid 250 during the photosynthesis period 450 would provide sufficient nutrients to support the productivity of the biofilm 146.

Exposure of the biofilm 140 to oxygen that diffuses into the photobioreactor enclosure 110 could retard the onset of the autofermentation period 460. To prevent oxygen diffusion, the photobioreactor enclosure 110 is constructed using flexible film that is substantially impermeable to oxygen. Film fabrication methods and film compositions that minimize oxygen diffusion are commercially available and known to those of ordinary skill in the art. Examples of substantially oxygen-impermeable flexible films that are commercially available are polyethylene, polyester, and barrier films such as 3M HB-P 69731, which comprises a polyester base film, a heat sealable ethylene vinyl acetate copolymer layer and a ceramic oxide coating.

The path of gas flow 230 through the photobioreactor enclosure 110 is primarily from the inlet part 120 to the exhaust vent 130, such that positioning the inlet port 120 and the exhaust vent 130 near the top edge 180 of the photobioreactor enclosure 110 may contribute to incomplete gas flow 230 through lower portions of the photobioreactor enclosure 110 and uneven distribution of carbon dioxide to the biofilm 140. Low concentrations of carbon dioxide in gas flow 230 used in the photobioreactor enclosure 110 may require delivery of large volumes of gas to the photobioreactor enclosure 110, resulting in significant energy costs. The combination of these effects may be mitigated by introducing one or more partitions 470 that channel gas flow 230 more evenly throughout the photobioreactor enclosure 110.

Figure 6:
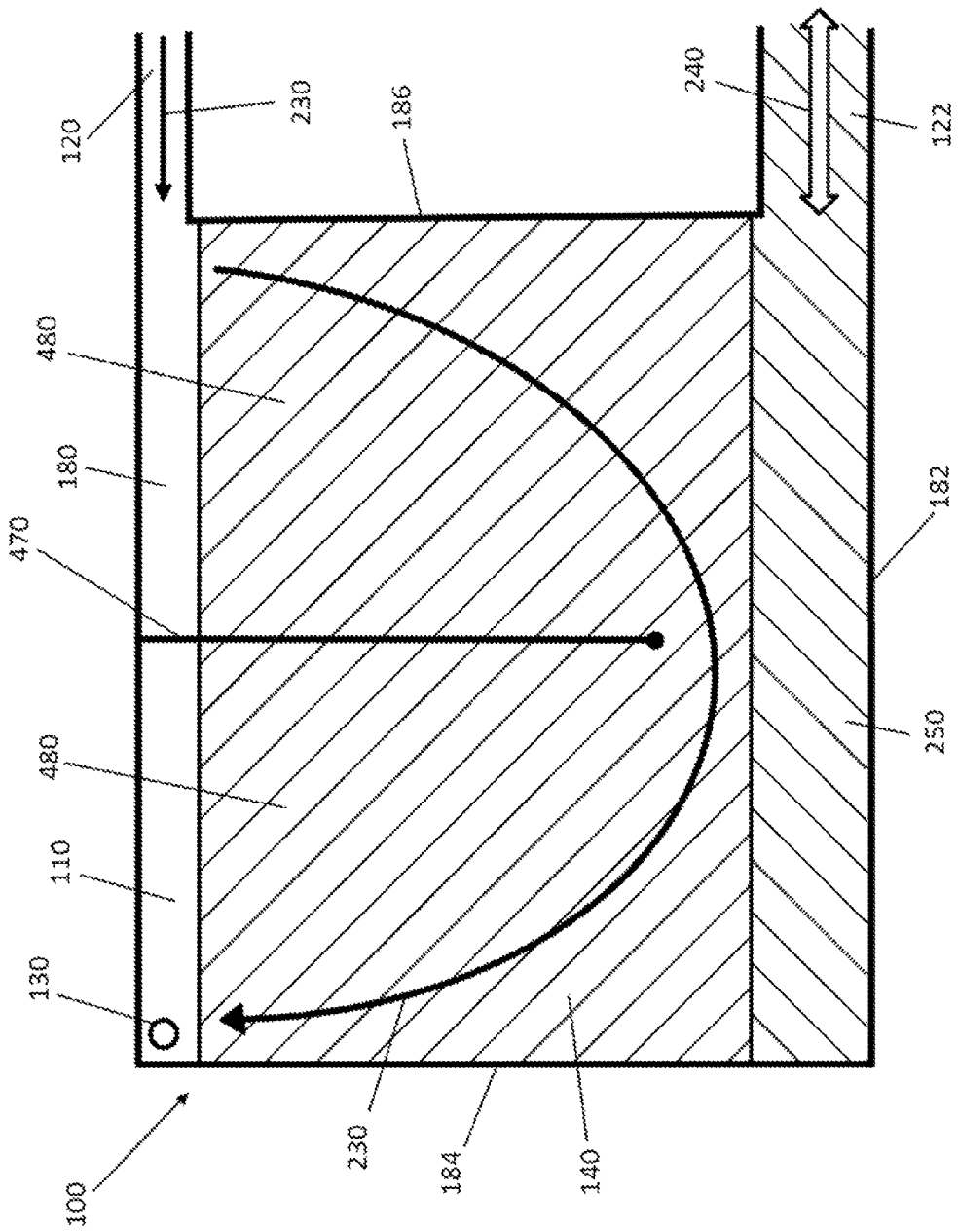
FIG. 6 shows a plan view of a flat panel biofilm photobioreactor design with a partition.

FIG. 6 shows an embodiment of a biofilm photobioreactor 100 that incorporates a partition 470 that directs gas flow 230 from the top edge 180 of the photobioreactor enclosure 110 toward the bottom edge 182, and back toward the top edge 180, where gas flaw 230 is expelled through the exhaust vent 130. The partition 470 and channels 480 may be created by the pattern of bonding plastic film in the body of the photobioreactor enclosure 110. This embodiment increases the uniformity of distribution of gaseous carbon dioxide in contact with the biofilm 140.

Figure 7:
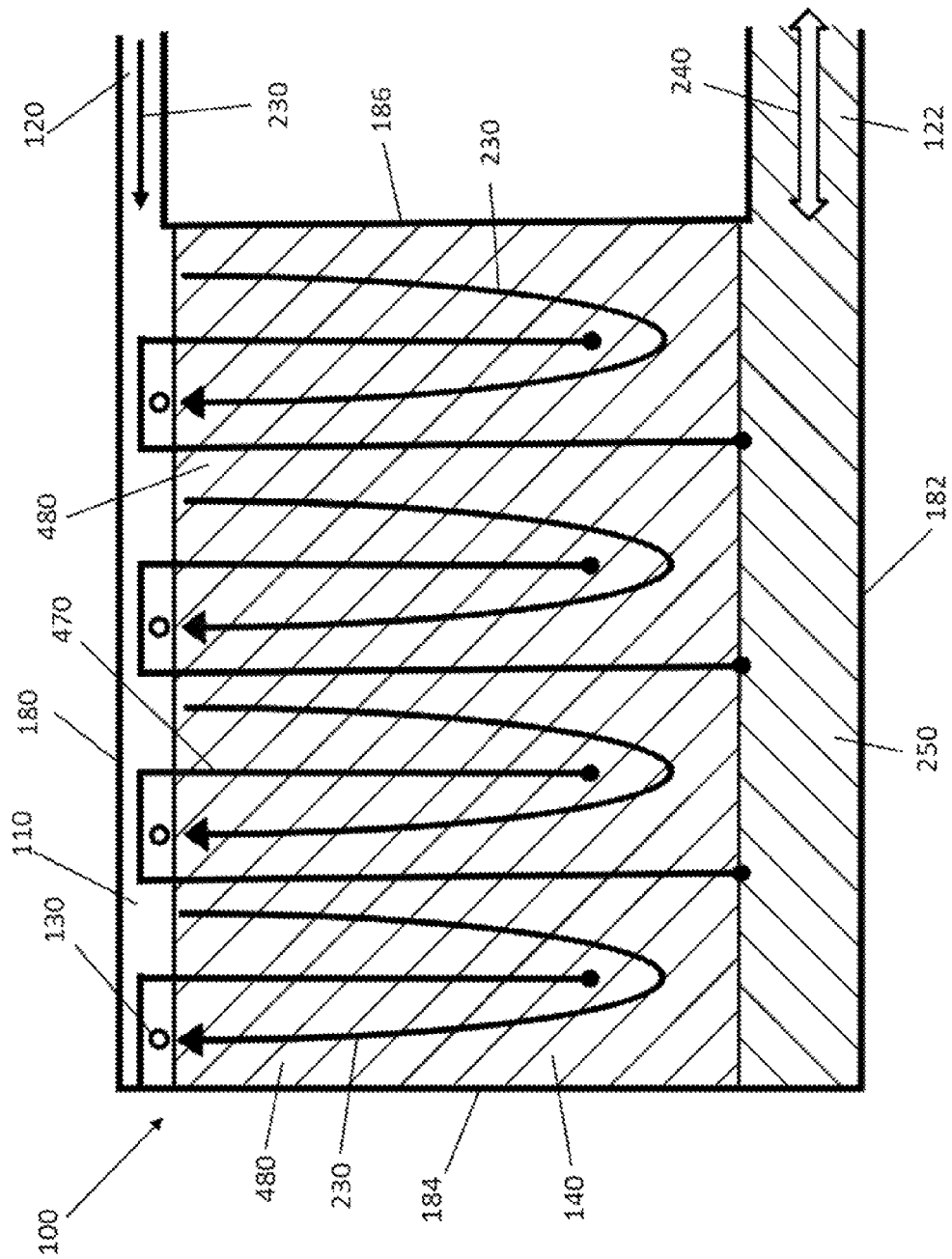
FIG. 7 shows a plan view of a flat panel biofilm photobioreactor design with multiple channels for flow of air and water.

FIG. 7 shows an embodiment of the biofilm photobioreactor 100 with multiple partitions 470 creating multiple U-shaped channels 480, a gas port 120 along the top edge 180 of the photobioreactor enclosure 110 and a liquid port 122 along the bottom edge 182 of the photobioreactor enclosure 110. The ports 120 and 122 direct gas flow 230 and liquid flow 240 to each channel 480. In this embodiment, the biofilm 140 is disposed on support substrates 150 positioned in the channels 480. The opposing walls 160 of the photobioreactor enclosure 110 are sealed together in a pattern forming the channels 480.

Biofilm 140 formation in the longer U-shaped channels 480 illustrated in FIG. 7 may be unevenly more dense closer to the gas port 120 and less dense closer to the exhaust vents 130. This effect occurs because the suitable organisms in the biofilm 140 consume most of the carbon dioxide in the gas flow 230 exiting the gas port 120 and produce a denser biofilm 140 in that location, while concentration of carbon dioxide in the gas flow 230 close to the exhaust vents 130 is significantly decreased providing less feedstock for suitable organisms in that location. Additionally, entering gas flow 230 may have low water content, resulting in drying of the biofilm 140 close to the gas port 120.

FIG. 8 shows an embodiment of the biofilm photobioreactor 100 with multiple partitions 470 creating multiple linear channels 480 that are greater in number and have shorter path lengths for gas flow 230 compared with the embodiment shown in FIG. 7. A combined port 124 located along the bottom edge 182 of the photobioreactor enclosure 110 supplies gas flow 230 and liquid flow 240 to the channels 480.

A biofilm 140 is disposed on support substrates 150 positioned in the channels 480. The support substrate 150 may be adhered to a wall 160 and/or edge 180, 182, 184 or 186 of the photobioreactor enclosure 110. Alternatively, the support substrate 150 may be attached to and suspended between the partitions 470 that form the channels 480 in the photobioreactor enclosure 110.

Biofilm 140 formation in the embodiment shown in FIG. 8 is more uniform, since the distribution of gas and carbon dioxide to more channels 480 and the shorter path lengths for gas flow 230 minimize discrepancies in the concentration of carbon dioxide between the combined port 124 and the exhaust vents 130, allowing the microorganisms to consume carbon dioxide and form a biofilm 140 that is distributed more evenly along the height of each channel 480. The increased number of channels 480, shorter gas flow 230 path lengths and increased exposure of the biofilm 140 to gas flow 230 help to increase uptake of carbon dioxide by the biofilm 140 and increase the removal of oxygen from the biofilm 140. Gas flow 230 enters the channels 480 at the bottom, so that liquid draining from the upper portions of the biofilm 140 helps to keep the biofilm 140 hydrated near the combined port 124.

Pressure inside the photobioreactor enclosure 110 increases when gas flow 230 is added to the photobioreactor enclosure 110 and when the photobioreactor enclosure 110 is filled with liquid 250. The internal gas or liquid pressure causes the walls 160 to deform outward. There may be distortion of the photobioreactor enclosure 110 shape so that exterior areas of the photobioreactor enclosure 110 are no longer substantially flat but instead exhibit creases formed in the flexible film. Such creases introduce resistance in the path of gas flow 230 through the channels 480 and necessitate the use of higher pressure to maintain satisfactory gas flow 230. This effect is more pronounced with plastic film that is thicker and less flexible. Such distortion and creasing may be lessened or prevented by heat sealing the opposing walls 160 at intermittent points to prevent outward deformation under pressure.

The increase in total weight when the photobioreactor enclosure 110 is filled with liquid 250 may require the use of sturdier and potentially more expensive materials to construct the photobioreactor enclosure 110 and/or use of a mounting system 510. The biofilm photobioreactor 100 may need to be mounted on a frame. The strength required of the frame depends on the weight of the biofilm photobioreactor 100 and the amount of tension that develops when the photobioreactor enclosure 110 is filled with gas or liquid. The determination of suitable designs and identification of materials based on biofilm photobioreactor 100 weight, wind loading and tension is well known to those skilled in the art.

Figure 9:
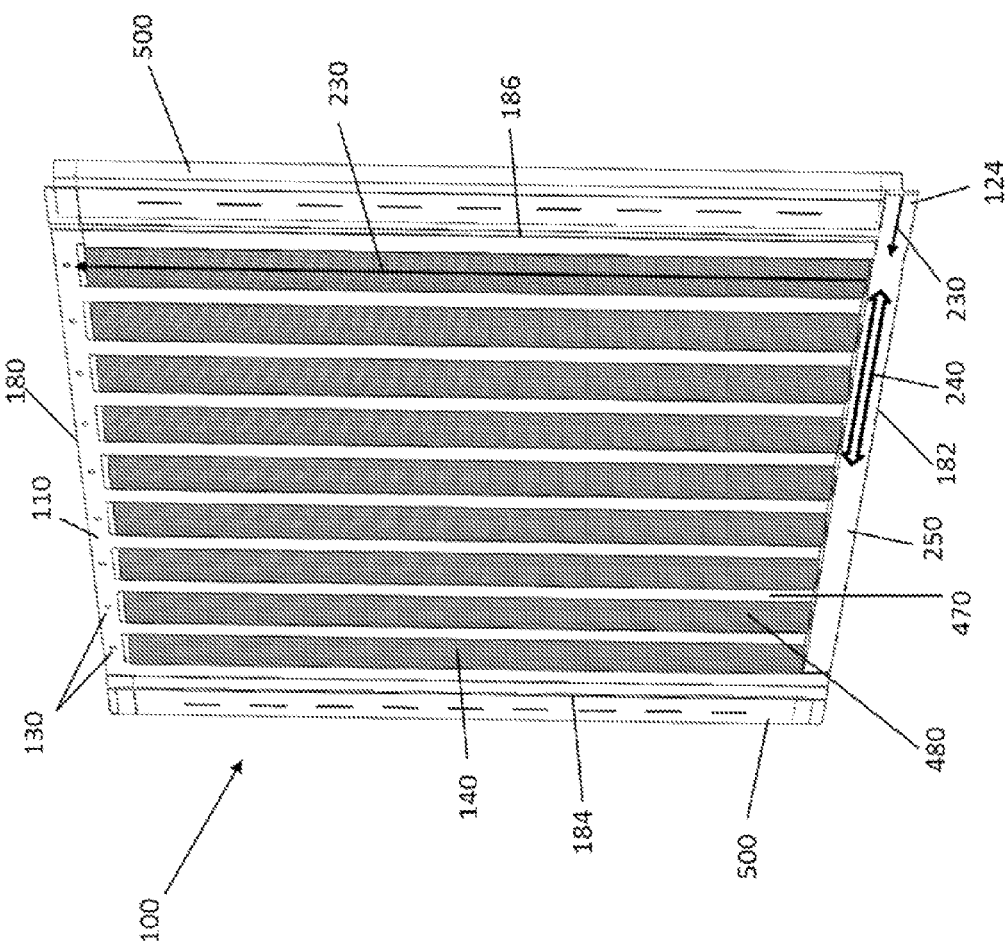
FIG. 9 shows a perspective view of a flat panel biofilm photobioreactor design with multiple channels for flow of air and water.

FIG. 9 illustrates an embodiment in which the photobioreactor enclosure 110 is attached to side supports 500. Exemplary side supports 500 are made of wood or any other material that is suitably rigid, lightweight and inexpensive. The photobioreactor enclosure 110 may be attached to side supports 500 by stapling any other suitable means of bonding or adhering.

Generally, a biofilm photobioreactor 100 of this design will retain its shape if it is held at the left and right edges 184 and 186 while the top and bottom edges 180 and 182 are left free. The internal pressure holds the channels 480 open and gives the structure sufficient stiffness to be self-supporting.

Photosynthetic microorganisms tend to operate best in a certain range of light intensity. Photosynthesis is most productive when the microorganisms are exposed to as much light as they can readily tolerate. Excessive light exposure can cause photoinhibition, leading, to loss of productivity. Light exposure also raises the temperature in a photobioreactor enclosure 110, which can cause loss of efficiency or cell death.

The rate of gas flow 230 within the photobioreactor enclosure 110 can also be adjusted to provide cooling, for example by controlling the voltage of the power source for the fan 190. In order to avoid expenses associated with providing liquid and moving gas, it is preferable to use a microorganism that tolerates and performs well at elevated temperatures, but it is possible to use the aforementioned methods to reduce peak temperatures so the microorganism used need not withstand such extremes of temperature as would be the case without heat management.

A biofilm photobioreactor 100 must be mounted in a position that allows exposure of the biofilm 140 to light. In a preferred embodiment, a biofilm photobioreactor 100 set up outdoors is mounted so that its position can be adjusted on at least one axis to track the position of the sun and control exposure to incoming solar radiation and radiant energy input. For example, a biofilm photobioreactor 100 set up in the Northern Hemisphere can be mounted so that the translucent wall 160 of the photobioreactor enclosure 110 faces south and the angle of the biofilm photobioreactor 100 can be adjusted. Alternatively, the biofilm photobioreactor 100 can face east, and its angle can be adjusted as the sun moves during the day so that a more or less constant light intensity is maintained by controlling the angle with respect to the sun.

Figure 10:
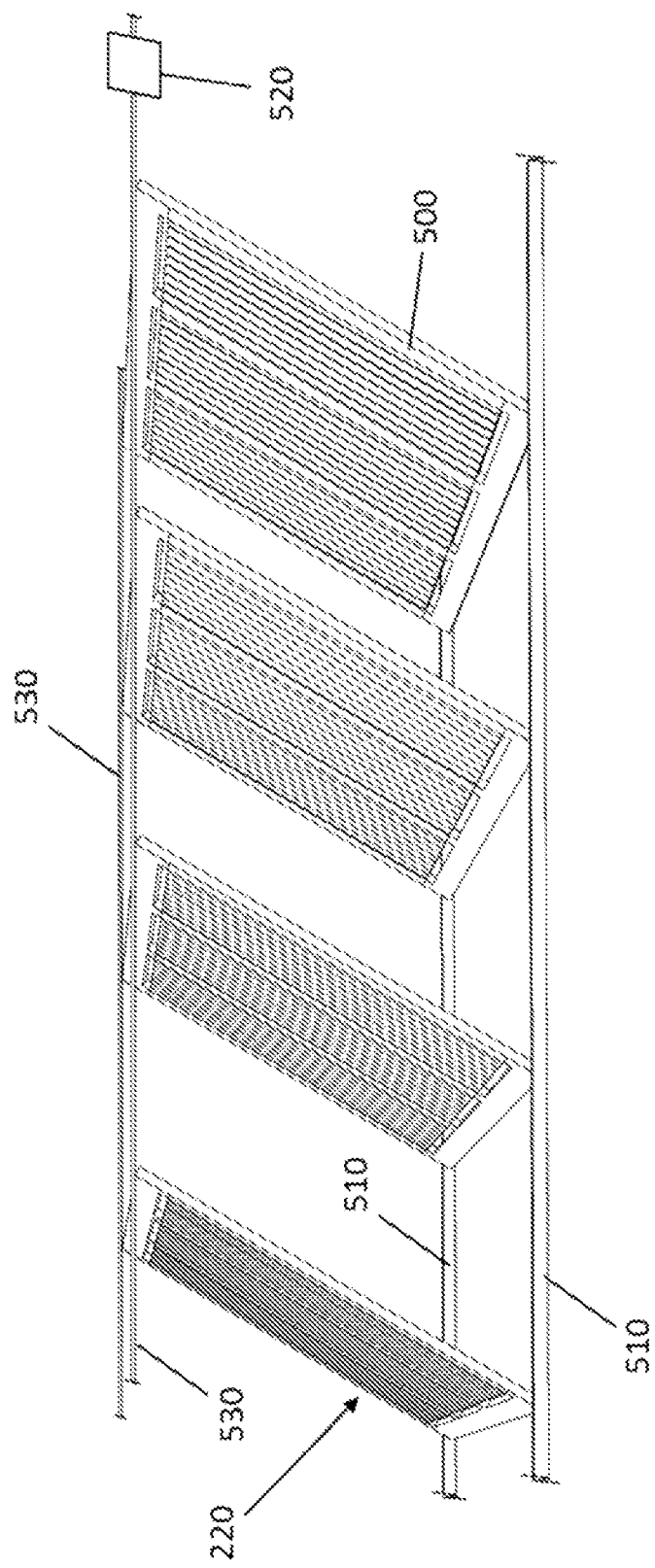
FIG. 10 shows a perspective view of an array of at panel photobioreactors and a mounting system.

FIG. 10 shows a mounting system 510 for an array 220 of biofilm photobioreactors 100 that incorporates a motor 520 to control the positions of adjustment arms 530. The mounting system 510 and adjustment arms 530 permit the angle of the biofilm photobioreactors 100 to be adjusted in order to optimize light exposure and photobioreactor 100 temperature. The angular disposition of the array 220 of biofilm photobioreactors 100 can be controlled in parallel, so individual mechanical mounting and controls are not required.

The mounting system 510 may allow adjustment of the angle of the biofilm photobioreactor 100 such that the photobioreactor enclosure 110 can be made substantially horizontal when it is filled with liquid, in order to limit deformation of the shape of the photobioreactor enclosure 110. Alternatively or in addition, the biofilm photobioreactor 100 can be mounted on a frame that exerts tension on the biofilm photobioreactor 100 if the shape of the photobioreactor enclosure 110 deforms excessively.

The mounting system 510 allows vertical orientation of the biofilm photobioreactor 100, which increases culture surface area that is exposed to sunlight per reactor ground footprint area and the culture per volume is exposed to sunlight. Vertical orientation of the biofilm photobioreactor 100 enhances distribution of culture within the light field and may be used to optimize light adaption and utilization by the biofilm 140 through ensuring that the biofilm 140 is consistently exposed to the same amount of light at each position in the photobioreactor enclosure 110.

The degree of deformation of the photobioreactor enclosure 110 shape relates to internal pressure in the photobioreactor enclosure 110 and the width of the channels 480. In general, narrow channels 480 prevent the biofilm photobioreactor 100 walls 160 from deforming excessively. Very narrow channels 480 require a greater internal pressure to open.

The degree of deformation of the photobioreactor enclosure 110 also relates to the distance between the left and right edges 184 and 186 of the photobioreactor enclosure 110. The distance between the left and right edges 184 and 186 of the photobioreactor enclosure 110 is maximal when it is completely flat, so if the photobioreactor enclosure 110 is mounted with this maximal distance between its left and right edges 184 and 186, deformation will be largely prevented. If the photobioreactor enclosure 110 does not deform, the channel 480 cross-section will be very small and gas will not flow freely. Furthermore, if there is any irregularity in the photobioreactor enclosure 110, some channels 480 or parts of channels 480 may not open at all, resulting in failure of gas flow 230 and loss of productivity in the affected channels 480. As a result, there is an optimal spacing of the left and right edges 184 and 186 of the photobioreactor enclosure 110 so that channels 480 open reliably and allow uniform gas flow 230.

During cycles in which the photobioreactor enclosure 110 fills with liquid, channels 480 must also open enough to allow uniform flow. It is not desirable for the channels 480 to open excessively, which would necessitate pumping more liquid to fill the channels 480. Further, during the autofermentation period, it is desirable to have a small volume of liquid in the channels 480 so that the change in concentration of the chemical product in the liquid is relatively large.

Given these considerations, a biofilm photobioreactor 100 can be mounted so that the distance between the left and right edges 184 and 186 can be adjusted by exerting a pulling force that is perpendicular to the longitudinal axes of the chambers. Stretching the biofilm photobioreactor 100 laterally in this manner will decrease the depth and volume of the channels 480 such that liquid volume in the channels 480 is reduced and product concentration is increased.

This embodiment provides a variation in the method of operating the biofilm photobioreactor 100. At the beginning of the autofermentation period 460, the photobioreactor enclosure 110 may be stretched laterally to increase the distance between the left and right edges 184 and 186, after which the channels 480 of the biofilm photobioreactor 100 are at least partially filled with liquid 250. The reduction in volume of liquid 250 needed to fill the stretched channels 480 during autofermentation 460 increases concentration of the chemical product in the liquid 250, which can facilitate recovery of the chemical product from the liquid 250. The reduction in volume of liquid 250 also reduces the quantity of dissolved oxygen and other electron acceptors that must be consumed by the biofilm 140 before conditions for autofermentation exist, which can decrease the time needed for autofermentation to begin. The reduction in volume of liquid 250 also reduces the total weight of liquid 250 in the photobioreactor enclosure 110. Decreased liquid 250 weight permits the use of lighter materials for construction of the biofilm photobioreactor 100, which helps reduce capital costs, and also helps reduce operating costs for liquid 250 and energy consumption.

The volume of the photobioreactor enclosure 110 that is not occupied by the biofilm 140 and the support substrate 150 can be adjusted. When the photobioreactor enclosure 110 is filled with gas or liquid 250, the fluid exerts pressure on the walls 160 of the photobioreactor enclosure 110, forcing them outward so each channel 480 has a rounded configuration. This outward deformation of the walls 160 of the channels 480 results in lateral contraction of the photobioreactor enclosure 110, bringing its left and right edges 184 and 186 closer together. In contrast, because the partitions 470 between channels 480 run from top to bottom, there is very little change in the distance between the top and bottom edges 180 and 182 of the photobioreactor enclosure 110 when it is filled with fluid 250.

The structure of the photobioreactor enclosure 110, regardless of how it is mounted, sets an upper limit on the degree to which the channel 480 volume can be increased and the photobioreactor enclosure 110 width (distance between left and right edges 184 and 186) can be decreased. In practice, it is preferable to mount the photobioreactor enclosure 110 in such a way that the left and right edges 184 and 186 of the photobioreactor enclosure 110 are constrained so that the decrease in photobioreactor enclosure 110 width, and hence the increase in photobioreactor enclosure 110 volume, is limited.

The preferred volume for the photobioreactor enclosure 110 is not necessarily the same for all phases of its operation. In particular, the opening of the channels 480 after draining the liquid 250 and initiating gas flow 230 is most reliable when the photobioreactor enclosure 110 volume is at least about two liters per square meter of photobioreactor enclosure 110 surface area.

During the period of autofermentation 460, the chemical product concentration that can be reached in a single night depends on the productivity of the biofilm 140 and the liquid 250 volume. The desired chemical product concentration depends on the economics of purification and the tolerance of the microorganism to the chemical product. Chemical product concentration must be high enough that the chemical product can be economically recovered, but low enough to avoid an unacceptable level of stress to the organism.

As an example, assume that ethanol can be economically purified from liquid 250 that is at least 0.5% ethanol by weight, and the microorganism used is tolerant of nightly exposure to ethanol of at most 1%. If the nightly conversion of carbohydrate to ethanol is 10 grams of carbohydrate per square meter, or about 5.1 grams of ethanol per square meter, then the total liquid 250 volume should be in the approximate range of 500 ml to 1 liter.

Table 1 shows chemical product concentration as a function of productivity and liquid 250 volume.

The total liquid 250 volume includes both the added medium and the liquid 250 bound in the biofilm 140 and the support substrate 150, so the added medium will be smaller than the total liquid 250 volume. If the volume of liquid 250 in the biofilm 140 is a large fraction of the total liquid 250 volume, it may be necessary to include a wash step after the autofermentation period 460 to recover an acceptable fraction of the chemical product.

The liquid 250 volume can also be reduced by withdrawing liquid 250, which allows the channels 480 to collapse so that the opposing walls 160 contact each other. This normally occurs every time the photobioreactor enclosure 110 is drained. The channels 480 open when gas flow 230 resumes.

The reliability of channel 480 collapse depends on the material chosen for construction of the photobioreactor enclosure 110. Flexible films are preferred to allow for reliable channel 480 collapse.

The liquid 250 volume that remains after channel 480 collapse generally is smaller than the desired volume described above, so this method is most appropriate if the desired volume is unusually small. Alternatively, the photobioreactor enclosure 110 can be oriented approximately horizontally. The channels 480 will collapse when gas flow 230 ceases and can be filled with liquid 250 in this position, but the fill volume is considerably less than the fill volume of a vertical photobioreactor enclosure 110.

If a microorganism has a high tolerance for the chemical product, or if productivity is low, it may not be convenient to reduce the liquid 250 volume sufficiently to achieve an economically desirable concentration of chemical product in a single night of autofermentation. If this is the case, it is possible to reuse the autofermentation medium 300 several times so the chemical product concentration is increased to the desired level.

If a microorganism has a low tolerance for the chemical product, or if productivity is very high, it may not be convenient to increase the liquid 250 volume sufficiently to prevent damage to the microorganism. If this is the case, the liquid 250 can be withdrawn after a limited time period to avoid excess chemical product concentration and new medium can be added to continue autofermentation.

A separate advantage of a low fermentation volume is that the period of time required for the biofilm 140 to reduce the

TABLE 1

|  |  | Total liquid volume per square meter | | | | | | |
| --- | --- | --- | --- | --- | --- | --- | --- | --- |
|  |  | 0.25 L | 0.5 L | 1 L | 2 L | 3 L | 4 L | 5 L |
| Ethanol | 2 g | 0.41% | 0.20% | 0.10% | 0.05% | 0.03% | 0.03% | 0.02% |
| productivty per square meter per day | 5 g | 1.02% | 0.51% | 0.26% | 0.13% | 0.09% | 0.06% | 0.05% |
|  | 10 g | 2.04% | 1.02% | 0.51% | 0.26% | 0.17% | 0.13% | 0.10% |
|  | 15 g | 3.07% | 1.53% | 0.77% | 0.38% | 0.26% | 0.19% | 0.15% |
|  | 20 g | 4.09% | 2.04% | 1.02% | 0.51% | 0.34% | 0.26% | 0.20% |
|  | 25 g | 5.11% | 2.56% | 1.28% | 0.64% | 0.43% | 0.32% | 0.26% |
|  | 30 g | 6.13% | 3.07% | 1.53% | 0.77% | 0.51% | 0.38% | 0.31% |
|  | 35 g | 7.16% | 3.58% | 1.79% | 0.89% | 0.60% | 0.45% | 0.36% |
|  | 40 g | 8.18% | 4.09% | 2.04% | 1.02% | 0.68% | 0.51% | 0.41% |

Desirable chemical product concentration values preferably are in the range of from about 0.50% to about 1.00%. The chemical product concentration values presented in Table 1 are exemplary, based on reasonable ranges for ethanol production. Chemical product concentration values will differ for other chemical products, other microorganisms, and other separation technologies; suitable calculations can be made by one of ordinary skill.

oxygen concentration sufficiently to induce autofermentation is decreased. For example, if an organism uses carbohydrate at the rate of 1 gram per square meter hour, it will consume oxygen at a rate of about 1 gram per square meter hour. A 1 liter volume will only have about 10 milligrams of oxygen, so the time to anoxia in this example is less than 1 minute.

In most cases, the considerations noted previously are more significant than time to anoxia in determining the opti mal water volume. Time to anoxia may be important if it is necessary to use large volumes and respiratory rates are low. Time to anoxia may also be reduced by pretreatment of the fermentation medium by degassing, for example by vacuum degassing or heat degassing, by chemical oxygen scavenging, by sparging, for example with nitrogen, or by biological processes such as bacterial growth in a closed container without aeration.

When autofermentation medium is stored, either between fermentations that reuse the same medium or if it is necessary to hold the product containing medium before it goes on to a product separation step, the fermentation medium can be held in conditions in which the amount of oxygen that can enter the stored medium is insufficient to allow a significant amount of biological degradation of the product to occur, for example in a closed tank with a limited or zero headspace.

Internal pressure stresses portions of flexible film that are sealed together, such as partitions 470, and potentially can induce mechanical failure. Accordingly, the film used to construct the photobioreactor enclosure 110, the size of the channels 480 and the operating pressure of the photobioreactor enclosure 110 must be selected to ensure that mechanical failure does not occur.

Another design consideration is that ports 120, 122 and 124 must be sized to avoid excessive head loss during periods of gas and liquid movement.

The biofilm photobioreactor 100 incorporates a control system to operate pumps 330, fans 190 and similar equipment for the purpose of adding and removing gas and liquid to and from the photobioreactor, as well as to operate motors 520 used to adjust a mounting system 510 if it is adjustable. The control system can use inputs such as wind speed, air temperature and light intensity to adjust the angle of the photobioreactors to achieve optimal biofilm photobioreactor 100 performance with respect to photosynthetic rate, biofilm photobioreactor 100 temperature and avoidance of mechanical failure due to wind loading.

It is advantageous for the biofilm 140 to have a high specific rate of fermentation. The rate of fermentation can be affected by medium constituents. Generally, the medium used during photosynthesis will be chosen to facilitate high photosynthetic efficiency and photosynthate accumulation, while the fermentation medium will be chosen to facilitate high fermentation rate. The fermentation medium will also be chosen to facilitate extraction of the chemical product from the medium.

The rate of fermentation is also determined by the characteristics of the microorganism in the biofilm 140 and its specific fermentation rate. Generally, fermentation rate in autotrophic microorganisms is related to the energy demands of the microorganism and the availability of food reserves. In order to obtain the greatest productivity for a given biomass, it is desirable for the specific fermentation rate to be high.

The process of fermentation can adversely affect the medium and cause accumulation of chemical products that are toxic to the biofilm 140 at elevated concentrations. Depending on the fermentation rate and the tolerance of the microorganism for accumulated chemical product(s), the liquid used during autofermentation may be extracted periodically from the photobioreactor enclosure 110 to harvest chemical product(s), and then the photobioreactor enclosure 110 may be refilled with fresh liquid. For example, if a biofilm 140 measuring 1 square meter has accumulated 20 grams of carbohydrate that it ferments to ethanol in 500 milliliters of water, then the resulting ethanol concentration will be slightly over 2%. If the organism tolerant of exposure to 1% ethanol but not 2%, then it is necessary to extract the medium containing the ethanol.

Medium in which chemical product is collected may be used in more than one autofermentation period before it is processed to extract the chemical product. The medium stored under anaerobic conditions prior to processing in order to protect the accumulated chemical product from aerobic heterotrophic microorganisms. After the medium is processed and the chemical product is extracted, the medium may be reused in successive autofermentation periods.

Autofermentation will not necessarily occur during every dark period. Instead of adding autofermentation liquid, the dark cycle can comprise flowing gas at a low flow rate through the photobioreactor enclosure 110, alternated with periodic, brief submersion of the biofilm 140 to assure sufficient hydration, similar to the daytime cycle. For example, if accumulation of metabolic intermediate compound(s) in the biofilm 140 is only 5 grams per square meter per day, the autofermentation medium volume is 500 milliliters of water, and the microorganism can tolerate 2% ethanol, then it is desirable to permit up to 4 days of accumulation of metabolic intermediate compound(s) before autofermentation is induced so that the autofermentation medium will reach the tolerance limit of the microorganism. Achieving a higher ethanol concentration before harvesting the ethanol is desirable because higher product concentration reduces purification costs.

Autofermentation also does not need to occur during the initial growth of the biofilm 140. Gas flow 230 may be maintained during dark conditions at a low rate with periodic immersion if necessary for hydration. Once the biofilm 140 is mature and ready to be productive, chemical product can be harvested by inducing autofermentation.

Example 1

Two biofilm photobioreactors, PBR 1 and PBR 2, were fabricated out of 3M Scotchpak HB-P 69731 Translucent High Barrier Film. This film was chosen due to its resistance to oxygen permeability and ease of use in prototype construction.

The photobioreactor enclosures each incorporated a gas port positioned near the top edge of the photobioreactor enclosure, a liquid port positioned near the bottom edge of the photobioreactor enclosure and partitions creating four "U" shaped channels, similar to the design shown in FIG. 7. Ambient air was introduced into the channels via the gas port using an aquarium pump with flow capacity of 2.25-4.50 liters per minute. The channels were fashioned so that air entered into the "U" via the gas port, flowed down through the "U" and then back up to an 18-20 gauge gas exhaust vent. Media were introduced and removed via the liquid port.

Support substrate fabric of woven polyester was seamed into each photobioreactor enclosure and acted as a substrate for biofilm development. Total surface area of each photobioreactor enclosure was 0.1428 square meters and the volume of each photobioreactor enclosure was 0.415 liters.

Operation of the biofilm photobioreactors consisted of a photosynthesis cycle during which glycogen was produced and stored, and an autofermentation cycle during which glycogen was catabolized. In photosynthesis cycles, a freshwater photosynthesis medium was pumped through the liquid port, filling the photobioreactor enclosure, and then the medium was immediately pumped through the liquid port from the photobioreactor enclosure to a storage reservoir.

In the autofermentation cycle, a nitrogen-sparged, freshwater autofermentation medium was pumped through the liquid port, filling the photobioreactor enclosure, and remained in the photobioreactor enclosure until just before the beginning of the photosynthesis cycle. The autofermentation medium was depleted of $SO_4$ and other terminal electron acceptors. No air was introduced into the photobioreactor enclosures during the autofermentation period. The process of regularly exchanging media and delivering air to the photobioreactors was automated using proprietary software that controlled peristaltic pumps and air pumps.

PBR 1 and PBR 2 were each inoculated with 15 μL culture of *Chroococcidiopsis* sp, into a 500 ml reservoir of marine BG-11, made with filtered seawater containing about 1-3% dissolved salts. The biofilm photobioreactors were mounted in front of cool white fluorescent lamps providing about 75 μmol photons per square meter per second at each photobioreactor surface. The photobioreactor enclosures were filled and immediately drained every 20 minutes.

Regular photosynthesis cycles were initiated every 30 minutes. The biofilm photobioreactors were maintained at about 27° C. with a 24-hour photoperiod at an irradiance of 75 μmol photons per square meter per second. The BG-11 medium was incrementally changed to the freshwater photosynthesis medium over the course of 12 days. After the media exchange was completed, light was adjusted to a 16-hr photoperiod.

Autofermentation cycles were initiated. The autofermentation cycles and nitrogen sparging were automated to provide nitrogen gas flow to the autofermentation medium reservoir for 1.5 hours before the autofermentation cycle was initiated by flooding the photobioreactor enclosure with the autofermentation medium. After several hours, the autofermentation medium was pumped out of the photobioreactor enclosure, and the photosynthesis cycle resumed. Automated autofermentation cycles occurred each day, with the photobioreactor enclosure placed in darkness through shading with black cloth.

After the autofermentation medium was pumped into each photobioreactor enclosure, initial samples for organic acids, ethanol, oxygen and pH were taken by gravity draining a small autofermentation medium aliquot from the photobioreactor enclosure. Organic acid samples (in duplicate) were filtered through a 0.2 μm syringe filter and stored at −80° C. until analysis. Ethanol samples (in duplicate) were aliquoted into gas chromatography (GC) vials and stored at −20° C. until analysis. Organic acid and ethanol samples were quantified less than 7 days from sampling. Dissolved oxygen and pH measurements were taken immediately using bench top probes. At the end of the autofermentation cycle, final samples were obtained as described above. Prior to automation, photobioreactors were sampled each time an autofermentation cycle was attempted. Once the photobioreactors were automated, sampling occurred three times per week.

Autofermentation cycle length varied from 4.5 to 21.5 hours. Oxygen ranged from 0.23 to 0.86 mg/L at the start of the autofermentation cycle. Initial concentrations of organic acids, lactate, acetate, and formate ions were very low or below detection limits in the medium at the beginning of the autofermentation cycle. At the end of the autofermentation cycles, oxygen ranged from 0.13 to 1.44 mg/liter. Organic acids were present at the end of the autofermentation cycle in all but one experimental trial, confirming autofermentation by *Chroococcidiapsis* sp. in biofilm photobioreactors. Organic acid yields, expressed as concentrations at the autofermentation cycle end, were highest in the longest duration cycle. Medium pH was variable but declined following, autofermentation.

Acetate was typically the most abundant organic acid produced during autofermentation, although both lactate and acetate were present at the autofermentation cycle end with concentrations ranging from 2 to 20.5 ppm. Formate was only detected in three trials in very low concentrations.

Figure 11:
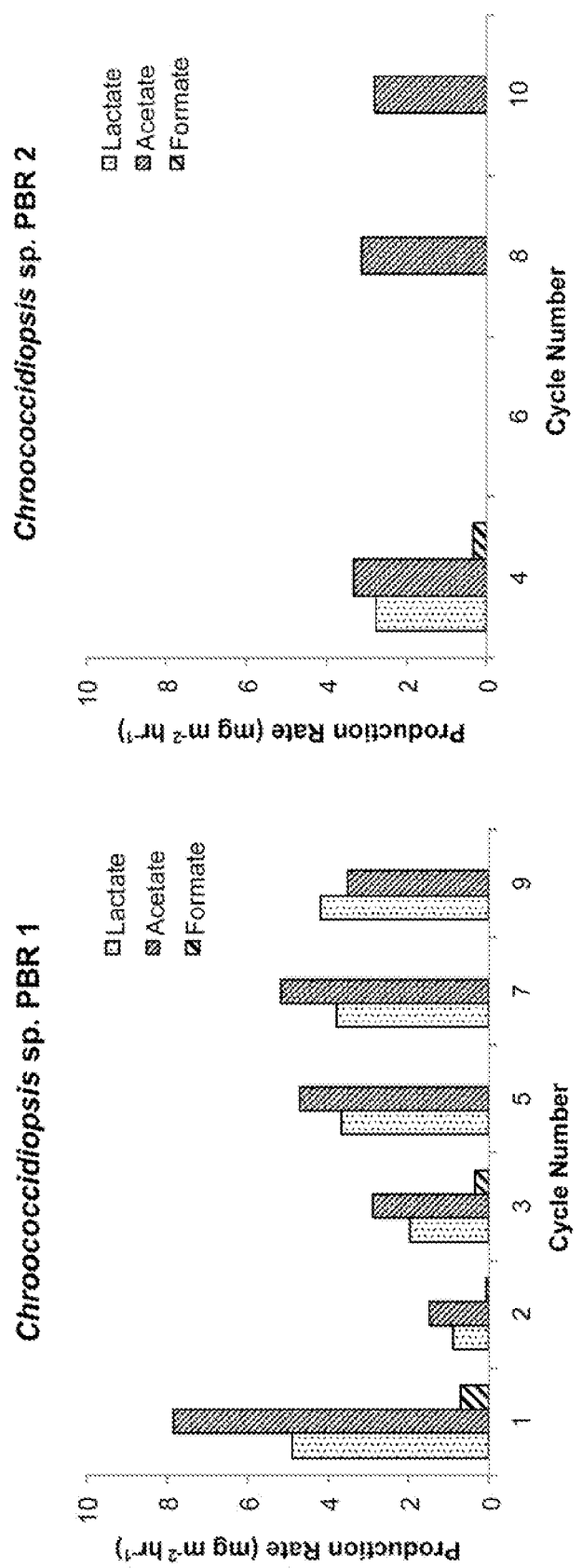
FIG. 11 shows organic acid production rates.

Assuming that concentrations reported as below the quantification limits ere effectively zero, organic acid production rates as a function of illuminated culture surface area (single sided illumination) were calculated using the following equation:

$$P=(C_{final}-C_{initial})/t \times PBR_{volume}/PBR_{illuminated\ area} \qquad \text{Eq. (1)}$$

where P is the production rate, $C_{final}$ and $C_{initial}$ are the final and initial organic acid concentrations, $PBR_{volume}$ is the biofilm photobioreactor volumetric capacity, $PBR_{illuminated}$ area is the biofilm photobioreactor surface area that is exposed to light (single-sided illumination) and t is time. Organic acid production rates were similar, with average values of 3.26 mg per square meter per hour for lactate and 3.93 mg per square meter per hour for acetate (FIG. 11). Formate production was extremely low.

Ethanol was measured on each occasion and was not detected in any sample.

Example 2

Two biofilm photobioreactors, PBR 3 and PBR 4, were fabricated out of 3M Scotchpak HB-P' 69731 Translucent High Barrier Film. Each photobioreactor enclosure incorporated a combination port for gas and liquid flow positioned near the bottom edge of the photobioreactor enclosure and partitions creating eight "I" shaped channels, similar to the design shown in FIG. 8. Ambient air was introduced into each channel via the combination port using an aquarium pump

TABLE 2

Autofermentation Cycle Data for PBR 1 and PBR 2

| | | | Beginning of Autofermentation Cycle | | | | | End of Autofermentation Cycle | | | | |
|---|---|---|---|---|---|---|---|---|---|---|---|---|
| PBR No. | Cycle (hrs) | Cycle Number | pH | $O_2$ (mg/L) | Lactate (ppm) | Acetate (ppm) | Formate (ppm) | pH | $O_2$ (mg/L) | Lactate (ppm) | Acetate (ppm) | Formate (ppm) |
| 1 | 6 5 | 1 | | 0.86 | 1.0 | 7.2 | 0.2 | | 0.58 | 12.0 | 24.8 | 1.8 |
| 1 | 6.2 | 2 | | 0.23 | <0.2 | 1.1 | <0.2 | | 0.13 | 2.0 | 4.3 | 0.2 |
| 1 | 21 5 | 3 | | 0.71 | <0.2 | <0.2 | <0.2 | | 0.65 | 14.6 | 21.4 | 2.5 |
| 2 | 21.5 | 4 | | 0.66 | <0.2 | <0.2 | <0.2 | | 0.49 | 20.5 | 24.7 | 2.6 |
| 1 | 4.5 | 5 | | 0.42 | <5 | <5 | — | 9.17 | 0.42 | 5.7 | 7.3 | — |
| 2 | 4.5 | 6 | | 0.39 | <5 | — | — | 9.13 | 1.44 | <5 | <5 | — |
| 1 | 5.5 | 7 | 7.65 | 0.64 | <5 | <5 | — | 6.92 | 0.76 | 7.2 | 9.8 | — |
| 2 | 5.5 | 8 | 9.11 | 0.65 | <5 | <5 | — | 7.90 | 0.63 | <5 | 5.9 | — |
| 1 | 6 | 9 | 7 32 | 0.50 | <5 | — | — | 6.50 | 1.05 | 8.7 | 7.3 | — |
| 2 | 6 | 10 | 9.06 | 0.75 | — | — | — | 7.91 | 1.42 | <5 | 5.8 | — | with flow capacity of 2.25-4.50 liters per minute. Air entered each channel from the bottom through the combination port and flowed up to an 18-20 gauge gas exhaust vent Media entered each channel and were removed via the combination port.

Support substrate fabric of woven polyester was seamed into each photobioreactor enclosure and acted as a substrate for biofilm development. Total surface area of each photobioreactor enclosure was 0.1428 square meters and the volume of each photobioreactor enclosure was 0.415 Titers.

Operation of the biofilm photobioreactors consisted of a photosynthesis cycle during which glycogen was produced and stored, and an autofermentation cycle during which glycogen was catabolized. Photosynthesis cycles were initiated by flushing each photobioreactor enclosure with freshwater photosynthesis medium. After the photobioreactor enclosures were filled and immediately drained through the combination port using the freshwater photosynthesis medium, ambient air was pumped through each photobioreactor enclosure using aquarium air pumps. Air exchange was the primary method of oxygen management. The freshwater photosynthesis medium flush occurred every 30 minutes during the 18-hr photosynthesis cycle.

Autofermentation cycles were initiated by turning off air flow to the photobioreactor enclosures, then pumping nitrogen-sparged, freshwater autofermentation medium into the photobioreactor enclosures through the combination port. The autofermentation medium was depleted of $SO_4$ and other terminal electron acceptors. The autofermentation medium was held in each photobioreactor enclosure for the duration of the 6-hr autofermentation cycle. The process of regularly exchanging media and delivering air to the photobioreactor enclosures was automated using proprietary software that controlled peristaltic pumps and air pumps.

PBR 3 and PBR 4 were each inoculated with 500 mL culture of *Geitlerinema* sp. into a 500 ml reservoir of marine BG-11. The biofilm photobioreactors were mounted in front of cool white fluorescent lamps providing about 75 μmol photons per square meter per second at each photobioreactor surface. The photobioreactor enclosures were filled and immediately drained every 30 minutes.

The biofilm photobioreactors were maintained at about 27° C. with a 16-hour photoperiod at an irradiance of 75 μmol photons per square meter per second. The marine BC-11 medium was incrementally changed to the freshwater photosynthesis medium over the course of 16 days.

Daily six-hour autofermentation cycles were initiated. One 24-hour autofermentation cycle was also completed.

After the autofermentation medium was pumped into each photobioreactor enclosure, initial samples for organic acids, ethanol, oxygen and pH were taken by gravity draining a small autofermentation medium aliquot from the photobioreactor enclosure. Organic acid samples (in duplicate) were filtered through a 0.2 μm syringe filter and stored at −80° C. until analysis. Ethanol samples (in duplicate) were aliquoted into gas chromatography (GC) vials and stored at −20° C. until analysis. Organic acid and ethanol samples were quantified less than 7 days from sampling. Dissolved oxygen and pH measurements were taken immediately using bench top probes. At the end of the autofermentation cycle, final samples ere obtained as described above.

Four autofermentation cycles were attempted in each of PBR 3 and PBR 4 (Table 3). During a 24-hour autofermentation cycle in PBR 4, the photobioreactor system developed a leak in the pump tubing and autofermentation medium drained from the photobioreactor enclosure. Consequently, no data are presented in Table 3 for that cycle.

TABLE 3

Autofermentation Cycle Data for PBR 3 and PBR 4

| | | | Beginning of Autofermentation Cycle | | | | | End of Autofermentation Cycle | | | | |
|---|---|---|---|---|---|---|---|---|---|---|---|---|
| PBR No. | Cycle (hrs) | Cycle Number | pH | $O_2$ (mg/L) | Lactate (ppm) | Acetate (ppm) | Formate (ppm) | pH | $O_2$ (mg/L) | Lactate (ppm) | Acetate (ppm) | Formate (ppm) |
| 3 | 6 | 1 | 9.82 | 2.71 | 1.05 | 1.01 | — | 9.06 | 1.0 | 0.78 | 12.51 | 0.44 |
| 4 | 6 | 2 | 9.15 | 1.05 | 1.22 | 0.95 | — | 8.58 | 1.28 | 7.27 | 33.21 | 1.90 |
| 3 | 6 | 3 | 9.74 | 0.96 | 1.06 | 1.04 | — | 9.13 | 0.81 | 3.28 | 10.20 | 0.88 |
| 4 | 6 | 4 | 9.43 | 0.83 | 0.78 | 1.02 | — | 8.82 | 1.20 | 3.67 | 28.73 | 0.88 |
| 3 | 24 | 5 | 9.53 | 1.21 | — | 1.32 | — | 8.55 | 0.4 | 2.14 | 21.77 | 4.62 |
| 3 | 6 | 6 | 9.11 | 1.24 | 0.98 | — | 1.26 | 8.66 | 0.81 | — | — | 3.05 |
| 4 | 6 | 7 | 9.02 | 0.96 | 3.20 | — | 1.36 | 8.51 | 0.78 | 1.29 | 2.51 | 3.52 |

Figure 12:
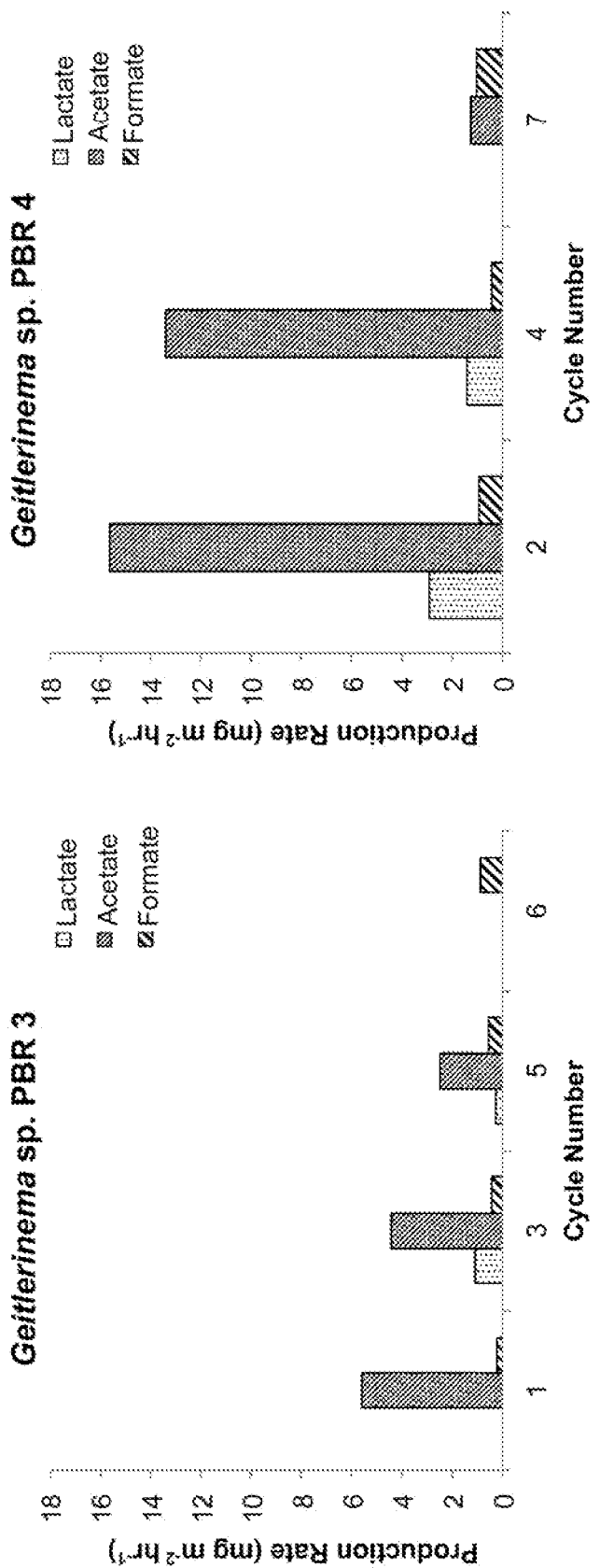
FIG. 12 shows organic acid production rates.

Production rates (standardized to illuminated area) were highest for acetate, with the exception of cycle 6 (FIG. 12). Lactate consumption was observed in cycles 1, 6 and 7. Formate production rates averaged 0.52 mg per square meter per hour ±0.27 mg per square meter per hour and 0.80 mg per square meter per hour ±0.33 mg per square meter per hour, respectively, for PBR 3 and PBR 4. Production rates for organic acids were higher in PBR 4 for all autofermentation cycles.

Figure 13:
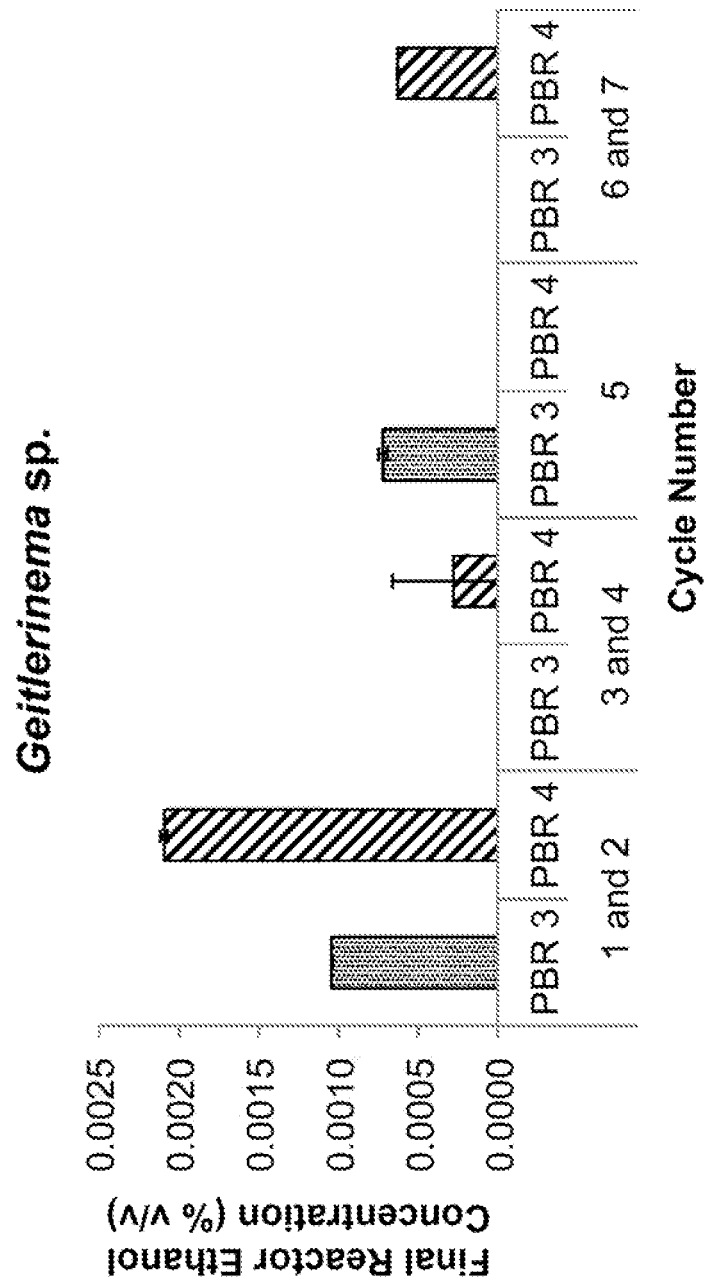
FIG. 13 shows final ethanol concentration achieved in a flat panel biofilm photobioreactor.

Ethanol was not detected in any samples at the start of any of the autofermentation cycles. However, low concentrations of ethanol were measured at the end of autofermentation cycles 1, 2, 4, 5 and 7 (FIG. 13). Final concentrations of ethanol in PBR 3 and PBR 4 ranged from 0.0002 to 0.0020% v/v.

Example 3

SEQ ID NO; 6 disclosed herein identify DNA sequences and protein sequences for a *Geitlerinema* sp. that is similar to the *Geitlerinema* sp. described in Examples 1 and 2, wherein the DNA sequences and protein sequences encode for enzymes that potentially are used to make ethanol from pyruvate through autofermentation.

TABLE 4

| SEQ ID NO | Sequence Type | Enzyme |
|---|---|---|
| 1 | DNA | Pyruvate dehydrogenase, E1-α |
| 2 | Encoded protein | Pyruvate dehydrogenase, E1-α |
| 3 | DNA | Pyruvate dehydrogenase, E1-β |

TABLE 4-continued

| SEQ ID NO | Sequence Type | Enzyme |
|---|---|---|
| 4 | Encoded protein | Pyruvate dehydrogenase, E1-β |
| 5 | DNA | Pyruvate dehydrogenase, E2 |
| 6 | Encoded protein | Pyruvate dehydrogenase, E2 |
| 7 | DNA | Alcohol dehydrogenase |
| 8 | Encoded protein | Alcohol dehydrogenase |
| 9 | DNA | Bifunctional alcohol dehydrogenase |
| 10 | Encoded protein | Bifunctional alcohol dehydrogenase |
| 11 | DNA | Acetyl-CoA synthetase |
| 12 | Encoded protein | Acetyl-CoA synthetase |
| 13 | DNA | Acetaldehyde dehydrogenase |
| 14 | Encoded protein | Acetaldehyde dehydrogenase |
| 15 | DNA | Acetatekinase |
| 16 | Encoded protein | Acetatekinase |

While the embodiments of the invention disclosed herein are presently considered to be preferred, various changes and modifications can be made without departing from the scope of the invention. The scope of the invention is indicated in the appended claims, and all changes that come within the meaning and range of equivalents are intended to be embraced therein.

What is claimed is:

1. A method of making at least one chemical product comprising the steps of:
    a) exposing a biofilm comprising a photosynthetic, autofermentative microorganism to light, wherein the biofilm is disposed on a support substrate that is disposed in channels of a biofilm photobioreactor and wherein the support substrate is fixed to inner surfaces of the biofilm photobioreactor,
    b) alternately flowing a gas comprising carbon dioxide through the channels and at least partially filling the channels with a first liquid, wherein the gas comprising carbon dioxide and the first liquid contact the biofilm and the photosynthetic, autofermentative microorganism makes at least one metabolic intermediate compound by photosynthesis;
    c) depriving the biofilm of light; and
    d) at least partially filling the channels of the biofilm photobioreactor with a second liquid, wherein the second liquid contacts the biofilm, the photosynthetic, autofermentative microorganism converts the at least one metabolic intermediate compound into the at least one chemical product and the at least one chemical product enters the second liquid.

2. The method of claim 1 further comprising the step of exerting a pulling force perpendicular to the longitudinal axes of the chambers before at least partially filling the chambers of the biofilm photobioreactor with a second liquid.

3. The method of claim 1 further comprising the step of extracting the second liquid containing the at least one chemical product from the biofilm photobioreactor.

4. The method of claim 1 further comprising the step of separating the at least one chemical product from the second liquid.

5. The method of claim 1 wherein the gas comprising carbon dioxide flows through the chambers for at least one time period of from about 5 minutes to about 4 hours.

6. The method of claim 1 wherein the chambers are at least partially filled with the first liquid for at least one time period of from about 10 seconds to about 20 minutes.

7. The method of claim 1 wherein the chambers are at least partially filled with the second liquid for a time period of from about 1 hour to about 18 hours.

8. The method of claim 1 wherein the second liquid is substantially depleted of electron acceptors.

9. The method of claim 1 further comprising the step of sparging the second liquid with nitrogen gas prior to at least partially filling the chambers of the biofilm photobioreactor with the second liquid.

* * * * *

UNITED STATES PATENT AND TRADEMARK OFFICE
CERTIFICATE OF CORRECTION

PATENT NO. : 8,691,538 B1  
APPLICATION NO. : 13/631478  
DATED : April 8, 2014  
INVENTOR(S) : Benjamin Moll et al.

Page 1 of 2

It is certified that error appears in the above-identified patent and that said Letters Patent is hereby corrected as shown below:

In the Claims

Column 53, line 44,  
Claim 1, delete "at least one chemical product" and insert --biofuel--.

Column 53, line 50,  
Claim 1, step a), insert --the-- before "inner".

Column 53, line 50,  
Claim 1, step a), delete "surfaces" and insert --surface--.

Column 53, line 54,  
Claim 1, step b), delete "liquid" and insert --medium--.

Column 53, line 58,  
Claim 1, step c), insert --subsequently-- before "depriving".

Column 53, line 58,  
Claim 1, step c), delete "and".

Column 53, line 59,  
Claim 1, step d), delete "at least partially filling the channels of the biofilm photobioreactor with a second liquid, wherein the second liquid contacts the biofilm, the photosynthetic, autofermentative microorganism converts the at least one metabolic intermediate compound into the at least one chemical product and the at least one chemical product enters the second liquid." and insert --removing the first medium; and--.

Signed and Sealed this  
Thirtieth Day of December, 2014

Michelle K. Lee  
*Deputy Director of the United States Patent and Trademark Office*

CERTIFICATE OF CORRECTION (continued)
U.S. Pat. No. 8,691,538 B1

Column 53, line 66,
Claim 1, add step e): --subsequently at least partially filling the channels of the biofilm photobioreactor with a second medium, wherein the second medium contacts the biofilm, and the photosynthetic, autofermentative microorganism converts the at least one metabolic intermediate compound into said biofuel which enters the second medium.--.

Column 54, lines 44, 46, 50, 55, 58, 60, 63 and 65,
Claims 2, 3, 4, 6, 7, 8, and 9, delete "liquid" and insert --medium--.

Column 54, lines 46-47, and 49,
Claims 3 and 4, delete "at least one chemical product" and insert --biofuel--.

UNITED STATES PATENT AND TRADEMARK OFFICE
CERTIFICATE OF CORRECTION

| | | |
|---|---|---|
| PATENT NO. | : 8,691,538 B1 | Page 1 of 1 |
| APPLICATION NO. | : 13/631478 | |
| DATED | : April 8, 2014 | |
| INVENTOR(S) | : Benjamin Moll et al. | |

It is certified that error appears in the above-identified patent and that said Letters Patent is hereby corrected as shown below:

In the Claims,
Column 53, line 53,
Claim 1, step b), delete "liquid" and insert --medium--.

Signed and Sealed this
Fourteenth Day of April, 2015

Michelle K. Lee
*Director of the United States Patent and Trademark Office*